US010689282B2

(12) United States Patent
Xu et al.

(10) Patent No.: US 10,689,282 B2
(45) Date of Patent: Jun. 23, 2020

(54) HYDROTHERMAL LIQUEFACTION CO-PROCESSING OF WASTEWATER SLUDGE AND LIGNOCELLULOSIC BIOMASS FOR CO-PRODUCTION OF BIO-GAS AND BIO-OILS

(71) Applicant: THE UNIVERSITY OF WESTERN ONTARIO, London (CA)

(72) Inventors: Chunbao Xu, London (CA); Laleh Nazari, London (CA); Madhumita B. Ray, London (CA)

(73) Assignee: THE UNIVERSITY OF WESTERN ONTARIO, London, ON (CA)

( * ) Notice: Subject to any disclaimer, the term of this patent is extended or adjusted under 35 U.S.C. 154(b) by 0 days.

(21) Appl. No.: 16/345,811

(22) PCT Filed: Oct. 27, 2016

(86) PCT No.: PCT/CA2016/051239
§ 371 (c)(1),
(2) Date: Apr. 29, 2019

(87) PCT Pub. No.: WO2018/076093
PCT Pub. Date: May 3, 2018

(65) Prior Publication Data
US 2019/0263700 A1    Aug. 29, 2019

(51) Int. Cl.
*C02F 11/04* (2006.01)
*C02F 11/18* (2006.01)
(Continued)

(52) U.S. Cl.
CPC .............. *C02F 11/04* (2013.01); *C02F 11/18* (2013.01); *C10G 1/086* (2013.01); *C11B 1/00* (2013.01);
(Continued)

(58) Field of Classification Search
CPC ........... C02F 11/04; C02F 11/18; C02F 11/10; C02F 2103/38; C11B 1/02; C11B 1/00;
(Continued)

(56) References Cited

U.S. PATENT DOCUMENTS 8,003,833 B2    8/2011 Appel et al.
9,404,063 B2    8/2016 Elliott et al.
(Continued)

OTHER PUBLICATIONS

International Search Report dated Jul. 26, 2017, in PCT/CA2016/051239 filed Oct. 27, 2016, 4 pages.
(Continued)

*Primary Examiner* — Fred Prince
(74) *Attorney, Agent, or Firm* — Hill & Schumacher

(57) ABSTRACT

This disclosure provides a process based on hydrothermal liquefaction (HTL) treatment for co-processing of high-water-content wastewater sludge and other lignocellulosic biomass for co-production of biogas and bio-crude oil. The mixture of waste activated sludge and lignocellulosic biomass such as birchwood sawdust/cornstalk/MSW was converted under HTL conditions in presence of KOH as the homogeneous catalyst. The operating conditions including reaction temperature, reaction time and solids concentration were optimized based on the response surface methodology for the maximum bio-crude oil production. The highest bio-crude oil yield of around 34 wt % was obtained by co-feeding waste activated sludge with lignocellulosic biomass at an optimum temperature of 310° C., reaction time of 10 min, and solids concentration of 10 wt %. The two by-products from this process (bio-char and water-soluble products) can be used to produce energy as well. Water-soluble products were used to produce biogas through Bio-methane Potential Test (BMP) and were found to produce around 800 mL bio-methane cumulatively in 30 days
(Continued)

per 0.816 g of total organic carbon (TOC) or 2.09 g of chemical oxygen demand (COD) of water-soluble products.

20 Claims, 8 Drawing Sheets

(51) Int. Cl.
    C10G 1/08    (2006.01)
    C11B 1/02    (2006.01)
    C12P 5/02    (2006.01)
    C11B 1/00    (2006.01)
    C02F 11/10    (2006.01)
    C02F 103/38    (2006.01)

(52) U.S. Cl.
    CPC ............... *C11B 1/02* (2013.01); *C12P 5/023* (2013.01); *C02F 11/10* (2013.01); *C02F 2103/38* (2013.01); *C10G 2300/1003* (2013.01); *C10G 2300/1014* (2013.01); *C10G 2300/4006* (2013.01); *C10G 2300/4012* (2013.01); *Y02E 50/343* (2013.01)

(58) Field of Classification Search
    CPC ....... C12P 5/023; Y02E 50/343; C10G 1/086; C10G 2300/1003; C10G 2300/1014; C10G 2300/4006; C10G 2300/4012
    USPC .................................................. 210/603, 631
    See application file for complete search history.

(56) References Cited

U.S. PATENT DOCUMENTS

| | | | |
|---|---|---|---|
| 10,538,447 B2* | 1/2020 | Pardo ................... | F23G 5/0276 |
| 2006/0096163 A1* | 5/2006 | Dickinson ............... | F23G 7/001 |
| | | | 44/552 |
| 2014/0128646 A1* | 5/2014 | Iversen ................... | C10G 1/04 |
| | | | 585/240 |

OTHER PUBLICATIONS

Azadi, P. et al., "Catalytic reforming of activated sludge model compounds in supercritical water using nickel and ruthenium catalysts", Applied Catalysis B: Environmental 134-135, (2013), pp. 265-273.
Neyens, E. et al., "Alkaline thermal sludge hydrolysis", Journal of Hazardous Materials B97, (2003), pp. 295-314.
Neyens, E. et al., "Advanced sludge treatment affects extracellular polymeric substances to improve activated sludge dewatering", Journal of Hazardous Materials 106B, (2004), pp. 83-92.
He, C. et al., "Conversion of sewage sludge to clean solid fuel using hydrothermal carbonization: Hydrochar fuel characteristics and combustion behavior", Applied Energy 111, (2013), pp. 257-266.
Kumar, V. et al., "Sludge: A waste or renewable source for energy and resources recovery?", Renewable and Sustainable Energy Reviews 25, (2013), pp. 708-728.
Molton, P.M. et al., "STORS: The Sludge-to-Oil Reactor System", EPA Project Summary, EPA/600/S2-86/034, (1986), 7 pages.
Kranich. W.L., "Conversion of sewage sludge to oil by hydroliquefaction", Technical Report PB-84-133768, OSTI. GOV, (1984), 2 pages.
Xu, C. et al., "Conversion of secondary pulp/paper sludge powder to liquid oil products for energy recovery by direct liquefaction in hot-compressed water", ScienceDirect, Water Research 42, (2008), pp. 1571-1582.
Kalogo, Y. et al., "State of Science Report: Energy and Resource Recovery from Sludge", WERF, (2008), 238 pages.
Nazari, L. et al., "Hydrothermal liquefaction of woody biomass in hot-compressed water: Catalyst screening and comprehensive characterization of bio-crude oils", Fuel 162, pp. 74-83, (2015).

Bradley, N., "The Response Surface Methodology", (2007), 84 pages.
Sahu, J.N. et al., "Response surface modeling and optimization of chromium(VI) removal from aqueous solution using Tamarind wood activated carbon in batch process", Journal of Hazardous Materials 172, (2009), pp. 818-825.
Vardon, D.R. et al., "Chemical properties of biocrude oil from the hydrothermal liquefaction of Spirulina algae, swine manure, and digested anaerobic sludge", Bioresource Technology 102, (2011), pp. 8295-8303.
Apha, "Standard Methods for the Examination of Water and Wastewater", 1010 A. Scope and Application of Methods, (1999), 1274 pages.
Tian, C. et al., "Hydrothermal liquefaction for algal biorefinery: A critical review", Renewable and Sustainable Energy Reviews 38, (2014), pp. 933-950.
Hang, H-J. et al., "Comparative studies of thermochemical liquefaction characteristics of microalgae, lignocellulosic biomass and sewage sludge", Energy 56, (2013), pp. 52-60.
Kuznetsov, B.N. et al., "Optimized methods for obtaining cellulose and cellulose sulfates from birch wood", Wood Sci Technol 49, (2015), pp. 825-843.
Shulga, G. et al., "Lignin Separated from the Hydrolyzate of the Hydrothermal Treatment of Birch Wood and its Surface Properties", Cellulose Chemistry and Technology 46 (506), (2012), pp. 307-318.
Daud, Z. et al., "Analysis the Chemical Composition and Fiber Morphology Structure of Corn Stalk", Australian Journal of Basic and Applied Sciences, 7(9), ISSN 1991-8178, (2013), pp. 401-405.
Flandez, J. et al., "Management of Corn Stalk Waste as Reinforcement for Polypropylene Injection Moulded Composites", BioResources 7(2), (2012), pp. 1836-1849.
Chen, H. et al., "Enzymatic Hydrolysis of Pretreated Newspaper Having High Lignin Content for Bioethanol Production", BioResources 10(3), (2015), pp. 4077-4098.
Zhang, L. et al., "Bio-crude production from secondary pulp/paper-mill sludge and waste newspaper via co-liquefaction in hot-compressed water", Energy 36, (2011), pp. 2142-2150.
Toor, S. S. et al., "Hydrothermal liquefaction of biomass: A review of subcritical water technologies", Energy 36, (2011), pp. 2328-2342.
Yin, S. et al. "Subcritical hydrothermal liquefaction of cattle manure to bio-oil: Effects of conversion parameters on bio-oil yield and characterization of bio-oil", Bioresource Technology 101, (2010), pp. 3657-3664.
Jazrawi, C. et al., "Pilot plant testing of continuous hydrothermal liquefaction of microalgae", Algal Research 2, (2013), pp. 268-277.
Cheng, S., "Bio-based Phenolic Resins and Adhesives Derived from Forestry Residues/Wastes and Lignin", (2011), 220 pages.
Vardon, D. R. et al., "Thermochemical conversion of raw and defatted algal biomass via hydrothermal liquefaction and slow pyrolysis", Bioresource Technology 109, (2012), pp. 178-187.
Matsui, T. et al., "Liquefaction of micro-algae with iron catalyst", Fuel, vol. 76, No. 11, (1997), pp. 1043-1048.
Speight, J.G. et al., "Handbook of Petroleum Analysis", (2001), 526 pages.
Yang, Y. et al., "Production of Bio-Crude from Forestry Waste by Hydro-Liquefaction in Sub-/Super-Critical Methanol", AIChE Journal vol. 55, No. 3, (2009), pp. 807-819.
Sun, P. et al., "Direct liquefaction of paulownia in hot compressed water: Influence of catalysts", Energy 35, (2010), pp. 5421-5429.
Zhang, L. et al., "Energy recovery from secondary pulp/paper-mill sludge and sewage sludge with supercritical water treatment", Bioresource Technology 101, (2010), pp. 2713-2721.
Li, S. et al., "Influence of temperature on pyrolysis of recycled organic matter from municipal solid waste using an activated olivine fluidized bed", Fuel Processing Technology 92, (2011), pp. 1776-1782.
Ross, A.B. et al., "Hydrothermal processing of microalgae using alkali and organic acids", Fuel 89, (2010), pp. 2234-2243.
Nazari, L. et al., "Hydrothermal liquefaction of woody biomass in hot-compressed water: Catalyst screening and comprehensive characterization of bio-crude oils", Fuel 162, (2015), pp. 74-83.

(56) References Cited

OTHER PUBLICATIONS

Peterson, A. A. et al., "Thermochemical biofuel production in hydrothermal media: A review of sub- and supercritical water technologies", Energy Environ. Sci. 1, (2008), pp. 32-65.

\* cited by examiner

HYDROTHERMAL LIQUEFACTION CO-PROCESSING OF WASTEWATER SLUDGE AND LIGNOCELLULOSIC BIOMASS FOR CO-PRODUCTION OF BIO-GAS AND BIO-OILS

FIELD

The present disclosure relates to co-production of biogas and high quality bio-crude oil from high-water-content wastewater sludge and lignocellulosic biomass using hydrothermal liquefaction (HTL) treatments.

BACKGROUND

Growing interest in renewable energies due to shrinking reserves of fossil fuels and climate change concerns have led to extensive research towards gaseous and liquid fuels production from renewable energy resources such as biomass and waste. Energy generation from municipal and industrial wastes such as wastewater sludge is also environmental friendly way to deal with large volume of waste disposal with the additional advantage of eliminating part of the indirect greenhouse gas emissions from energy crops-derived biofuels [1]. Municipal and industrial wastewater treatment plants generate a large volume of waste activated sludge (WAS) as a result of biological treatment of the wastewater. This produced sludge poses a threat to the environment and needs further treatment prior to disposal or incineration [2]. Sludge handling and management costs may be as high as 25-50% of the total cost of the wastewater treatment process [3]. Recently there has been a rising interest in developing more environmentally friendly processes to reduce the volume of the sludge for disposal and replacing the conventional sludge disposal methods such as landfill disposal and incineration by converting sludge into bio-energy.

Improved management of biosolids has been identified as a targeted research area in the Canada-wide Strategy for the Management of Municipal Wastewater Effluent. Endorsed by the Canadian Council of Ministers of the Environment, it is aligned with the rising interest in environmentally friendly processes to reduce the volume of sludge for disposal and find methods of utilizing the matter to produce bioenergy and more valuable products.

There are numerous drop-in biofuel technologies under development globally. The most advanced processes operating at commercial scale generally require relatively clean, dry, and homogenous feedstocks such as virgin vegetable oils, algal oil, waste animal fats, and used cooking oil. Neste Oil is a global leader in hydroprocessing vegetable oils to hydrocarbon liquid fuels, with commercial scale plants operating in Finland, the Netherlands, and Singapore for a total production capacity of approximately 2 million tonnes per year. Pyrolysis technology is also being commercialized using woody biomass as feedstock. The initial product, often referred to as pyrolysis oil or bio-oil, can be used as lower grade heating oil or can be upgraded to industry standard hydrocarbon liquid fuels. KiOR has a commercial plant operating in Mississippi producing 40,000 tonnes per year of gasoline, diesel, and heating oil. Envergent Technologies, a Honeywell company, uses Ensyn's rapid thermal process (RTP®) technology also for conversion of woody biomass to pyrolysis oil. BTG-BTL company in the Netherland has also developed and commercialized BTL (biomass-to-liquid) pyrolysis process that converts up to 70 wt. % of the biomass feedstock into bio-oil and the remaining part into char and gas. (See https://www.btg-btl.com/en/technology).

Hydrothermal liquefaction (HTL) is a thermo-chemical depolymerization process used to convert wet biomass into crude—like oil—sometimes referred to as bio-oil or bio-crude under moderate temperature and high pressure developed to produce energy from biomass in the presence of water to avoid the energy-intensive prior drying [4]. It is a promising technology for converting waste biomass with high water content into value-added products, mainly bio-crude oil and solid residue (bio-char) in the absence of oxygen at 150-450° C. and pressure up to 25-30 MPa [5]. It eliminates the need of a costly de-watering/drying process that is otherwise required in other thermal/thermo-chemical processes. The remarkable properties of water such as low dielectric constant and high ionic product, play important roles as a solvent in liquefaction. The process can be made self-sufficient in energy using a part of the produced oil and char to provide heat for the HTL process.

The reaction typically uses homogeneous and/or heterogeneous catalysts to improve the quality of the produced products and yields. The carbon and hydrogen of the organic starting material, such as, but not limited to, biomass, low-ranked coals (lignite) and peat are thermo-chemically converted into hydrophobic compounds with low viscosity and high solubility. Depending on the processing conditions, the resulting fuel can be used as is for heavy engines such as rail or marine based engines, or the output may be upgraded to transportation fuels, including jet-fuel, diesel and regular gasoline.

HTL technology offers several advantages to the emerging fast pyrolysis process. While the process operating pressure for HTL is higher, the lower temperature and the ability to utilize wet sludge are the critical advantages. It has been found to be cost-effective compared to incineration [6] and can achieve additional benefit of pathogen reduction meeting the stringent regulation on sludge land applications. Further, the quality of the produced bio-oil is higher, with lower water content (5%), lower oxygen content (20-30%), and higher energy content or heating value (30-35 MJ/kg). By utilizing wet organic waste solids, our HTL technology would represent a significant advancement to the biofuels industry mainly through the ability to utilize readily available high moisture organic waste.

Currently there is only a single sludge-to-oil technology established or under development for energy recovery from wastewater sludge based on hydrolysis and hydrothermal treatment. An early study of sewage sludge liquefaction was performed by Kranich and Eralp [7]. Sewage sludge was converted to oil at different reaction temperatures in the presence of hydrogen as a reducing gas and catalysts such as $Na_2CO_3$, $NiCO_3$, and $Na_2MnO_4$. The oil yields were less than 20 wt % with water as the reaction medium [7], [8]. A pilot scale study was carried out by Molton et al. where primary and undigested sludge with 20% total solids (TS) were heated at 300° C. and 10 MPa pressure in a continuous reactor with 30 L/h flow rate and hydraulic retention time of 90 minutes. The technology was patented as sludge-to-oil reaction system (STORS) with oil yields ranging from 10-20 wt % and char from 5-30 wt % [5], [6]. It was commercialized by ThermoEnergy Company in 2005; however, there is currently no full-scale installation in operation.

Another competitive process for sludge processing is anaerobic digestion and biogas production and there are two commercial processes in operation. The Cambi process consists of three vessels (a pulping vessel, hydrolysis reactor, and a flash tank) and treats sludge under pressure at temperatures between 160-180° C. Cambi installations are now operating in Norway, Denmark, England, Ireland, Scotland, and Poland. The technology is relatively complex: solids from wastewater treatment must be dewatered to 16% dry solids prior to the process and a medium-pressure steam supply is required. Reports of odor problems have been associated with the process [9].

The BioThelys process is used to treat sludge with a solids concentration higher than 10% and operates at 150-180° C. and 8-10 bars pressure. Two full-scale facilities have been operating in France since 1998. Like the Cambi process, the BioThelys process may also be subject to odor concerns [9].

SUMMARY

Disclosed here is the bio-crude oil and bio gas production from the combination of waste activated sludge (WAS) and lignocellulosic biomass as a co-feed. Since WAS has high water percentage (>90%), lignocellulosic biomass was added to increase the solids concentration and to enhance the economics of the wastewater liquefaction. The operating conditions such as temperature, reaction time, and solids concentration were optimized using Central Composite Design (CCD) method. Based on a previous catalyst screening study performed by the authors[10], potassium hydroxide (KOH) was used as a homogenous catalyst in the process. The mixture of waste activated sludge and lignocellulosic biomass such as such as birchwood and rubber wood sawdust/cornstalk/MSW was converted under HTL conditions in presence of KOH as the homogeneous catalyst. The operating conditions including reaction temperature, reaction time and solids concentration were optimized based on the response surface methodology for the maximum bio-crude oil production. The highest bio-crude oil yield of around 34 wt % was obtained by co-feeding waste activated sludge with lignocellulosic biomass at an optimum temperature of 310° C., reaction time of 10 min, and solids concentration of 10 wt %. Comparison of this bio-oil with the bio-oil previously produced from sawdust in the same operating conditions showed a significant improvement in the molecular weight of the bio-crude, indicating the presence of lighter components. Comprehensive characterization of the bio-crude oil products showed that these bio-oils had lower thermal stability, higher volatile matter and lower fixed carbon contents and higher fractions of low boiling point compounds that resulted in their lower molecular weight.

In an embodiment there is provided a process for coproduction of biogas and bio-crude oil, comprising:

a) mixing wastewater sludge with waste lignocellulosic biomass to form a mixture with an overall solid content in a range from about 5 to about 25 wt %;

b) subjecting the mixture to hydrothermal liquefaction in a reactor at held at a temperature in a range from about 200 to about 350° C. under pressure in a range from about 50 to about 150 bars and in the presence of a catalyst to give a reaction product;

c) removing and collecting solid bio-char from the reaction product in the reactor, removing and collecting bio-oil from the reaction product in the reactor, and removing and collecting aqueous products from the reaction product in the reactor; and d) anaerobically digesting the aqueous products to produce and collecting biogas produced from the anaerobically digested aqueous products.

In an embodiment of the process the mixture of wastewater sludge and waste biomass may have a solid content in a range from about 8 to about 20 wt %.

In an embodiment of the process the solid content of the mixture of wastewater sludge and waste biomass may be about 10 wt %.

In an embodiment of the process the temperature may be maintained in a range from about 280 to about 330° C.

In an embodiment of the process the pressure may be maintained in a range from about 100 to about 150 bars.

In an embodiment of the process the catalyst may be any one or combination of KOH, $K_2CO_3$, NaOH, $Na_2CO_3$, Colemanite, $FeSO_4$, $Ca(OH)_2$, hydrotalcite (HT), and MgO.

The present process may be carried out in either a batch mode or in a continuous mode of operation.

A further understanding of the functional and advantageous aspects of the present disclosure can be realized by reference to the following detailed description and drawings.

BRIEF DESCRIPTION OF THE DRAWINGS

Embodiments of the method disclosed herein will be more fully understood from the following detailed description thereof taken in connection with the accompanying drawings, which form a part of this application, and in which.

DETAILED DESCRIPTION

Figure 1:
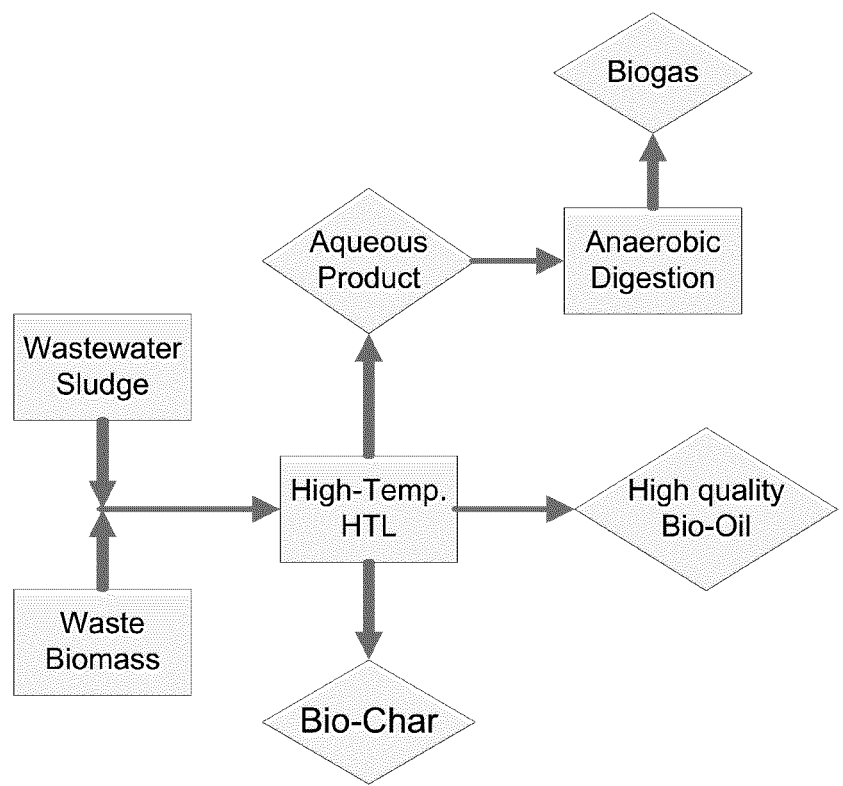
FIG. 1 shows a block diagram of the process disclosed herein.

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

As used herein, the terms, "comprises" and "comprising" are to be construed as being inclusive and open ended, and not exclusive. Specifically, when used in the specification and claims, the terms, "comprises" and "comprising" and variations thereof" mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about" and "approximately" are meant to cover variations that may exist in the upper and lower limits of the ranges of values, such as variations in properties, parameters, and dimensions. In one non-limiting example, the terms "about" and "approximately" mean plus or minus 10 percent or less.

As used herein, the phrase "biogas" means primarily one or both of methane ($CH_4$), carbon dioxide ($CO_2$), however it will be understood that biogas is a mixture of mostly methane and carbon dioxide with traces amounts of other gases such as nitrogen, hydrogen, hydrogen sulfide and oxygen.

As used herein, the phrase "bio-crude oil" or simply "bio-crude" or "bio-oil", is an oily product from hydrothermal liquefaction of biomass (or bio-feedstock). It is a high viscosity liquid (or solid-like) condensate recovered by hydrothermal treatment of biomass at elevated pressures and temperatures and a residence time range of a few minutes to hours in the absence of oxygen.

As used herein, the phrase "wastewater sludge" generally refers to the solid residue from the wastewater stream (municipal or industrial) produced in different steps during the treatment of the effluent, such as primary or secondary treatments. Wastewater sludge can also include other high-water containing biomass such as, but not limited to, wet harvested algal biomass.

As used herein, the phrase "waste biomass" means various type of lignocellulosic biomass such as forestry residues, municipal solid waste, wood waste and agricultural residues or waste.

The following provides materials and methods commonly used in the Examples.

Materials

Birch wood and rubber wood sawdust was supplied from a local lumber mill in London Ontario. Cornstalks were obtained from a local farm. The raw material was milled into particles having an average size less than 20 mesh. Used newspaper collected locally was employed as the waste newspaper. The collected waste newspaper was soaked in water for 24 hours (h), and then crushed into pulps with a domestic-use blender. The pulps were then dried at 105° C. for 12 h, grounded with a Wiley Mill into particles <20 mesh, and stored for future use. The waste activated sludge (WAS) was collected from Adelaide Pollution Control Plant, London, Ontario. The WAS samples were taken from rotary drum thickeners and stored at 4° C. prior to the experiments. The catalyst used in the experiments was potassium hydroxide (KOH) purchased from Sigma-Aldrich and was used as received.

While the catalyst could be KOH, $K_2CO_3$, NaOH, $Na_2CO_3$, Colemanite, $FeSO_4$, $Ca(OH)_2$, hydrotalcite (HT), and MgO, the most economically viable catalysts may be any one or combination of KOH, $K_2CO_3$, NaOH and $Na_2CO_3$.

A.C.S. reagent-grade acetone, used as reactor rinsing/washing solvent for product separation, was purchased from Caledon Laboratory Chemicals and was used as received.

Experimental Setup

The experiments were conducted in batch and continuous flow reactors.

Figure 2:
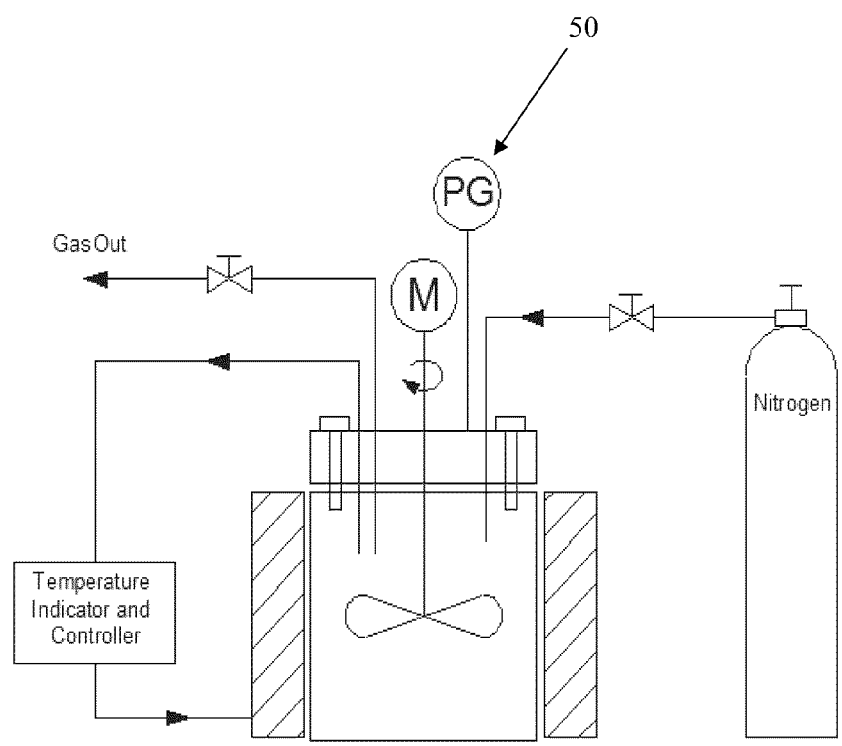
FIG. 2 shows a schematic diagram and photo of the 100 and 500 mL batch reactor.
Figure 2:
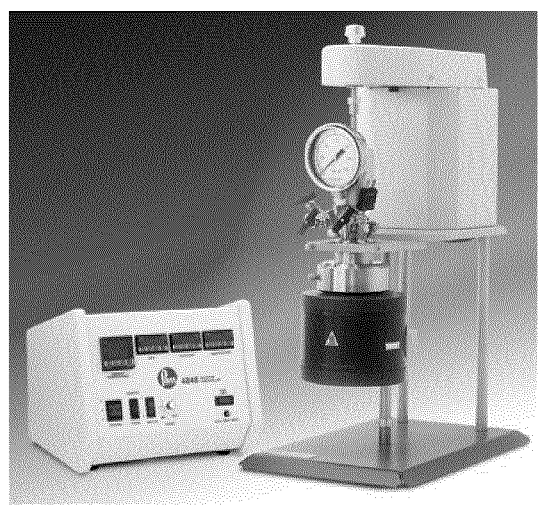

Examples 1 to 4 were performed in batch reactors. The batch reactors are a 100 mL and 500 mL stirred reactors 50 (Parr 4590 and 4570 Micro Bench top reactor), equipped with a mixer (M), heater, thermocouple, temperature controller and pressure gage (PG), see FIG. 2. For each experiment, appropriate amount of lignocellulosic biomass was added to 40 g WAS (making solid concentration of 5-15 wt % on a dry and ash-free basis) and the mixture was charged into the reactor together with KOH (5 wt % of total solids) as a homogeneous catalyst, chosen based on a previous catalyst screening study conducted by the authors [10]. Since WAS contained about 96 wt % water, no external water was added to the reaction mixture as solvent. The reactor 50 was then sealed and the residual air inside was removed by purging with nitrogen for at least five times. Then the reactor 50 was pressurized to 2 MPa using nitrogen and then heated under stirring to the desired temperature (200-350° C.). As soon as the reactor 50 reached the reaction temperature, it was hold at that temperature for the required retention time (10-60 min). Thereafter, the reaction was stopped by quenching the reactor 50 in a water/ice bath. Same procedure was followed for the experiments at optimum operating conditions.

Figure 3:
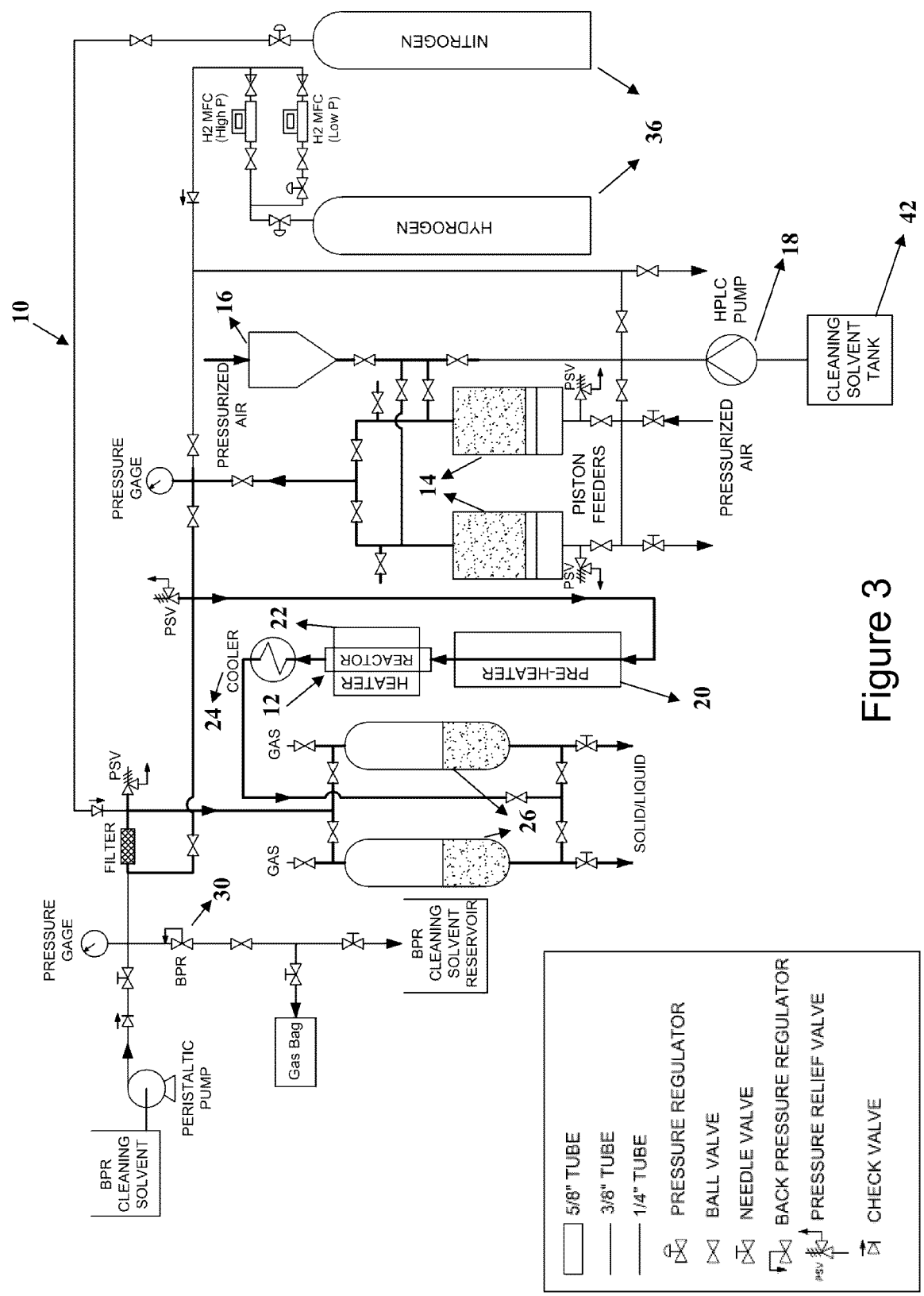
FIG. 3 shows a schematic diagram of a non-limiting embodiment of a continuous flow reactor used to carry out the present process.

Example 5 was performed in continuous flow reactor. The continuous reactor setup was designed and constructed for the present process. FIG. 3 shows the schematic diagram of this continuous flow reactor system 10 for hydrothermal liquefaction. The main parts of the system include a ⅝-inch SS316L tubular reactor 12, two piston feeders 14, feed tank 16, HPLC pump 18, pre-heater 20 and heater 22, coolers 24, two gas-liquid separation vessels 26 and back pressure regulator 30. The feed tank 16 is charged with the prepared slurry, and it is filled into the piston feeders 14 using compressed air. The feed is then injected into the reactor 10 by pumping using piston feeders 14 driven by high-pressure water supplied from the HPLC pump 18. Then the system is pressurized by nitrogen from tanks 36 and heated by heaters 20 and 22 to reach to the desired temperature. The pressure is adjusted through the backpressure regulator 30 to the desired pressure. After passing the reactor 10, the feed will be cooled in a cooler, is passed through separation vessel 26 and flashes. The gas will leave the separation vessel 26 from the top and solid/liquid products will be collected from the bottom of the vessels 26. The system is given enough time (approximately 2 hrs) to reach the desired temperature and steady-state operation. The feed from the first piston feeder 14 is used for the process stabilization and the effluent is collected in the first separation vessel 26. Once the operating conditions are stabilized, the piston feeders 14 are switched to feed the reactor 10 from the other piston feeder 14. The HTL products are collected in the second separation vessel 26.

For the experiments in continuous flow reactor, in order to prevent the adhesion of the bio-oil products to the reactor walls and clogging of the reactor, ethanol was used as a co-solvent in water for in-situ extraction of bio-oil or reaction intermediates by the solvent. The feedstock was prepared by mixing 1000 g of sludge, wood sawdust (mass ratio of sawdust to sludge was 0.15:1 (w/w)), 1.4 g KOH (5 wt % of substrate on a dry, ash-free basis) and 30 wt % ethanol with respect to the total weight of reaction mixture including ethanol and WAS. To facilitate pumping the co-feed of WAS and wood sawdust with high solids concentration, sodium carboxymethyl cellulose (CMC) was added to the feedstock slurry at an amount of 3 wt % of the total reaction mixture to obtain a uniform suspension. The feed had 12 wt % ash-free solids concentration.

Products Separation Procedure

After the reactor 50 was cooled down to room temperature the gas in the reactor 50 was collected into a 1.0 L gasbag for GC-TCD (Agilent Micro-GC 3000) analysis (120 mL air was injected into the gasbag as an internal standard). Then the reactor 50 was opened and the solid/liquid products were removed from the reactor 50 and transferred to centrifuge tubes 40. They were centrifuged at 4500 rpm for 10 minutes and filtered under vacuum through pre-weighed 0.45 μm glass fiber filter papers. The filtrate was collected as the water-soluble product (WSP). The reactor 50 was then rinsed with reagent-grade acetone from cleaning solvent tank 42 to completely remove any remaining materials including bio-crude oils and the residual chars adhering on the inner reactor wall by scraping with a spatula. The slurry and rinsing acetone were collected and filtered under vacuum through the 0.45 μm glass fiber retaining the water insoluble solids on it. The total solid residue was rinsed with acetone until the produced filtrate became colorless. The total solid residue was then oven dried at 105° C. overnight to constant weight to determine the yield of solid residue (SR) and biomass conversion while the filtrate was evaporated under reduced pressure to remove acetone at 50° C. in a rotary evaporator, and the dark color product left was weighed and designated as bio-crude oil.

Batch Reaction

For the batch reaction, the yields of the products are then calculated based on dry, ash-free (daf) initial biomass as following:

$$\text{Yield of Bio oil (wt \%)} = \frac{\text{Mass of bio-crude oil (g)}}{\text{Mass of } daf \text{ biomass (g)}} \times 100 \quad (1)$$

$$\text{Yield of } SR \text{ (wt \%)} = \frac{\text{Mass of solid residue-ash (g)}}{\text{Mass of } daf \text{ biomass (g)}} \times 100 \quad (2)$$

$$\text{Yield of Gas (wt \%)} = \frac{\text{Mass of produced gas (g)}}{\text{Mass of } daf \text{ biomass (g)}} \times 100 \quad (3)$$

$$\text{Yield of } WSP \text{ (wt \%)} = \quad (4)$$
$$100 - (\text{Yield of bio oil} + \text{Yield of gas} + \text{Yield of } SR)$$

Continuous Flow Reaction

For the continuous flow reaction, the yields were calculated as: The yields of the HTL products are then calculated based on dry, ash-free (daf) initial biomass as following:

$$\text{Yield of Bio oil (wt \%)} = \frac{m_b \text{ (g)}}{m_f^o \left(\frac{\text{ml}}{\text{min}}\right) \times c_f \left(\frac{\text{g}}{\text{ml}}\right) \times t(\text{min})} \times 100 \quad (5)$$

$$\text{Yield of } SR \text{ (wt \%)} = \frac{m_{SR} \text{ (g)}}{m_f^o \left(\frac{\text{ml}}{\text{min}}\right) \times c_f \left(\frac{\text{g}}{\text{ml}}\right) \times t(\text{min})} \times 100 \quad (6)$$

$$\text{Yield of Gas (wt \%)} = \frac{m_g \text{ (g)}}{m_f^o \left(\frac{\text{ml}}{\text{min}}\right) \times c_f \left(\frac{\text{g}}{\text{ml}}\right) \times t(\text{min})} \times 100 \quad (7)$$

$$\text{Yield of } WSP \text{ (wt \%)} = \quad (8)$$
$$100 - (\text{Yield of bio oil} + \text{Yield of gas} + \text{Yield of } SR)$$

where $m_b$ is the mass of bio-oil, $m_f^o$ is the mass flowrate of the feed (1.86 ml/min), $c_f$ is the concentration of dry, ash-free (daf) solids in the feed, t is the reaction time inside the reactor, $m_{SR}$ is the daf mass of solid residue and $m_g$ is the mass of produced gas.

Design of Experiments

Experimental design was performed using Response Surface Methodology (RSM). RSM is a statistical method for modeling and analysis of a problem using quantitative data from experiments to determine model equations by regression. This method optimizes the responses to variations of process parameters [11], [12]. The Central Composite Design (CCD) is one of the most popular RSM designs useful for building second order (quadratic) and third order (cubic) models for the response variables. A general form of the quadratic equation can be expressed as following [12]:

$$Y = b_0 + \Sigma_{i=1}^n b_i X_i + \Sigma_{i=1}^n b_{ii} X_i^2 + \Sigma_{i=1}^n \Sigma_{j>1}^n b_{ij} X_i X_j \quad (9)$$

Where Y is the response, $b_0$ is the constant coefficient, $b_i$, $b_{ii}$ and $b_{ij}$ are the linear, interaction and quadratic coefficients, and $X_i$, $X_j$ are the coded values of the independent variables, respectively [12]. In the present work, a standard CCD design with three variables was applied in order to study the effects of three independent variables (temperature, time and solids concentration) on bio-oil yields. The design contains 8 cubic points, 6 axial points, and 1 center point with 6 replicates for the center point. Thus a total of 20 experiments were performed. The center point replicates were chosen as a measure of precision. The variables levels were in the range of 200-350° C. for temperature, 10-60 min for reaction time, and 5-15 wt % for solids concentration. The factors and levels are presented in Table 1. For statistical calculations, the variable xi was coded to Xi according to the following relationship:

$$x_i = \frac{Hi + Lo}{2} + X_i \frac{Hi - Lo}{2} \quad (10)$$

Where Hi is the un-coded high level and Lo is the un-coded low level of a specific variable.

The design matrix was analyzed using Design Expert (version 7) and Minitab (version 17) software and the optimization was performed to maximize the bio-oil yield. Molecular weight (Mw) of the oils and yields of other products such as solid residue, WSP, and gas were also determined to explore the effect of different operating conditions on products yield.

Analysis of Products

Elemental analysis of the raw materials and products was performed on a Flash EA 1112 analyzer, employing 2,5-Bis (5-tert-butyl-benzoxazol-2-yl) thiophene (BBOT) as the calibration standard. The composition of the oxygen was estimated by difference. The heating value was calculated based on Dulong's formula (HHV=0.3383C+1.422(H–%)) where C, H, and O are the mass percentages of carbon, hydrogen and oxygen, respectively [13]. The compositions of gaseous products were determined using gas chromatograph equipped with a thermal conductivity detector (GC-TCD Agilent Micro-GC 3000). The bio-crude oil products were analyzed by Waters Breeze gel permeation chromatography (GPC-HPLC) instrument (1525 binary pump, UV detector set at 270 nm, Waters Styragel HR1 column at 40° C.) for their average molecular weight and polydispersity index (PDI) using THF as the eluent at a flow rate of 1 mL min$^{-1}$ with linear polystyrene standards for the molecular weight calibration curve. The average molecular weights were obtained from the GPC profiles for the bio-crude oil products. They were also analyzed by a gas chromatograph-mass spectrometer [GC-MS, Agilent Technologies, 5977A MSD) with a SHRXI –5MS column (30 m×250 μm×0.25 μm) and a temperature program of 60° C. (hold for 2 min)→120° C. (10° C./min)→280° C. (8° C./min, hold for 5 min)] for identifying the composition of bio-crude oils. The samples were diluted to 0.5% (g/g) with acetone and filtered (pore size 0.45 μm) to remove particles before analysis. The 1 μl sample was injected with a split ratio of 10:1. Compounds in the heavy oil were identified by means of the NIST Library with 2011 Update.

Thermal gravimetric (TGA) analysis, volatile matter (VM) and fixed carbon (FC) contents were determined by PerkinElmer Pyris 1 TGA in a nitrogen and air atmosphere. The samples were heated from 40° C. to 900° C. with a heating rate of 10° C. $min^{-1}$ and then burned with air at 900° C. for 20 minutes. The gas flow rate was 20 mL $min^{-1}$. A total organic carbon (TOC) analyzer (Shimadzu TOC-ASI) was used to measure the total organic carbon content in water-soluble products.

Total solids (TS), volatile solids (VS), and total oxygen demand (TCOD) of water-soluble product were performed according to the Standard Methods [14]. The moisture content and ash contents were determined based on ASTM E1756-08 (drying the samples at 105° C. for at least 12 hours) and ASTM E1755-1 (heating the samples at 575° C. for three hours) respectively.

The pH of WAS sample was determined by using the pH probe of SI Analytics potentiometric titrator. The Fourier transform infrared spectrometer (FT-IR) analyses were conducted on a PerkinElmer FT-IR spectrometer and the spectra were recorded in the region of 4000-550 $cm^{-1}$.

The chemical composition of the ashes was determined using inductively coupled plasma (ICP-AES). The solid samples underwent an acidic digestion with nitric acid and sulfuric acid at 90° C. for 1 hour. They were then cooled to ambient temperature followed by filtration and dilution prior to ICP analysis. During the ICP test samples were heated up to 6000-8000 K in order to vaporize and ionize the metallic compounds to be quantified: Na, K, Mg, Ca, Mn, Fe, Zn, Al and Si. The ions were detected and analyzed by atomic emission spectrometry.

Biochemical Methane Production Test

Biochemical methane potential (BMP) was measured using an AMPTS II (Bioprocess Control, Sweden). The batch anaerobic reactors were seeded with digestate (VS ~1.1%) collected from a local municipal anaerobic digester and fed with substrate at a substrate to inoculum ratio of approximately 1:3 on a mass VS basis. The volumes of WSP (substrate) and anaerobic seed were approximately 50 and 450 mL, respectively. Seed alone was used for the blank BMP tests. The BMP test was conducted for approximately 30 days and then stopped.

Feedstock Characterization

The physiochemical characteristics of the feedstock samples are given in Table 2. The proximate analysis of the feedstocks shows that birchwood sawdust had the highest overall volatile matter content on a dry weight basis (83.5%) compared to newspaper (76.1%), cornstalk (74.1%) and WAS (62.2%). The organic matter of lignocellulosic biomass is mostly comprised of lignin, cellulose and hemicelluloses, while it is mostly proteins, lipids and carbohydrates for wastewater sludge. In contrast to volatile matter, the ash content of waste activated sludge was as high as 23.67% compared to negligible amount of ash for sawdust (0.23%), 10.7% in cornstalk and 9.2% newspaper, respectively. The inorganic minerals in the ash were analyzed by ICP-AES and the results are shown in Table 3. The analysis shows that the main constituents of the ash fraction were calcium, potassium and magnesium for the lignocellulosic biomass and iron and calcium for the waste activated sludge.

The elemental analysis of the feedstocks shows that nitrogen concentration in sludge was higher in comparison to lignocellulosic biomass most likely due to the presence of proteins. Proteins also contain sulfur, and there are some sulfur-containing amino acids, such as methionine and cysteine [15]. Hence, nitrogenous and sulfur compounds (formed due to thermal degradation of proteins) could be expected in the liquefaction products. For all of the samples the molar ratio of H/C and O/C ranged from 1.57-1.65 and 0.48-0.75, respectively with low high heating values (HHV) of 14.6-16.9 MJ/kg.

Example 1

Experimental design studies were performed using the mixture of WAS and sawdust (BS-WAS). The optimization was performed to maximize the bio-oil yield using a standard CCD design. Since higher concentrations of the feedstock are more beneficial from the waste utilization point of view, a constraint of $X_3>10$ wt % was applied to the optimization process. The recommended optimal operating conditions were validated using experimental data (two replicate experiments) as presented in Table 4. The experimental and predicted values are in good agreement indicating good predictability of the model.

Example 2

Mixture of cornstalk and waste activated sludge (CS-WAS) was liquefied at the obtained optimum operating conditions in Example 1 (310° C. of temperature, 10 min reaction time and 10 wt % of substrate concentration in presence of KOH as the homogeneous catalyst). The yields of products, percentage of conversion and molecular weight of bio-crude oils are given in Table 5.

Example 3

A mixture of newspaper and waste activated sludge (NP-WAS) was liquefied at the obtained optimum operating conditions in Example 1 (310° C. of temperature, 10 min reaction time and 10 wt % of substrate concentration in presence of KOH as the homogeneous catalyst). The yields of products, percentage of conversion and molecular weight of bio-crude oils are given in Table 6.

Comparing the products yields from Examples 1 to 3, BS-WAS and CS-WAS produced the highest amount of bio-oil with the CS-WAS resulting in the lowest amount of solid residue and consequently the highest conversion rate. As a general trend the conversion rate for different biomass constituents under HTL conditions is in the order of lipids>proteins>carbohydrates [16]. Low conversion of carbohydrates is mainly due to higher hemicellulose and lignin contents. The lower bio-oil yield for NP-WAS explained by the higher carbohydrate content which has lower conversion efficiency. Typically, newspaper has higher percentage of cellulose and lignin compared to cornstalk and sawdust [17]-[22]. This is also confirmed by TGA analysis of the feedstocks that will be discussed later in the next sections. The highest conversion rate of the experiment with CS-WAS could also be due to the lowest lignin content of cornstalk (7.3-16%) [17], [18] compared to two other lignocellulosic biomass. Previous research shows that hydrothermal processing of lignin increases solid production since lignin depolymerization is subsequently followed by re-polymerization or self-condensation [23], [24].

The higher conversion rate for CS-WAS may also be attributed to the presence of inorganic materials in the cornstalk ash that can play the role of a catalyst for increased conversion and result in a reduced solid residue yields. The mineral salts may accelerate secondary depolymerization of intermediate products and prevent the formation of solid residue. As previously presented in Table 2, the ash content of cornstalk and newspaper are much higher compared to the sawdust. The analysis of the ash showed that cornstalk has the highest percentage of potassium compared to other feedstocks. The presence of potassium has been reported to be effective for suppressing solid yields during hydrothermal liquefaction. Potassium carbonate can result in reduced solid residue while potassium hydroxide can promote water-gas shift reaction [23], [25]. Sodium salts can also increase bio-crude oil yield and suppress char formation however, their activity is less than potassium salts [23]. Minor elements such as Fe or Ni may have also contributed to the reduced solid yields of the experiment with the mixture of cornstalk and WAS.

Example 4

The oil yields from liquefaction of only birchwood sawdust (BS) or WAS are listed in Table 7 for comparison. Comparing the oil yields from BS and WAS with the one from BS-WAS (Example 1) shows that addition of sawdust to WAS has no synergetic effect on oil yield. However, the key finding is that if additional lignocellulosic biomass, such as sawdust, cornstalk, MSW, is added as a co-feed to the wastewater sludge, the biocrude oil produced will have a lower molecular weight and higher energy content than the bio-oil produced using lignocellulosic biomass alone, which indicates synergistic and advantageous effects of co-liquefaction of lignocellulosic biomass and wastewater sludge.

Example 5

A mixture of rubber wood sawdust and waste activated sludge was liquefied at the obtained optimum operating conditions in Example 1 (310° C. of temperature, 10 min reaction time in presence of KOH as the homogeneous catalyst). The solid concentration was increased to 12% to examine the flowability of the slurry at a higher concentration. The yields of products, percentage of conversion and molecular weight of bio-crude oils are given in Table 8.

Characteristics of Bi-Oils Produced in Examples 1 to 4

Molecular Weight

The molecular weights of the bio-crude oils were measured by GPC and were in the range of 448-562 g/mole for the bio-oils from mixtures with the lowest molecular weight of 448 g/mole for CS-WAS sample. In a previous HTL experiment conducted by the authors [10] sawdust was used as a feedstock at almost the same operating conditions (KOH as the catalyst, 300° C. temperature, 10 wt % solids concentration and 30 min. reaction time). The molecular weight of this bio oil was found to be 856 g/mol. Compared to this, the mixture of WAS and lignocellulosic biomass has led to a much lower molecular weight of the oils and hence lower viscosity. The molecular weight of CS-WAS oil is also lower compared to the bio-oils from sludge or sawdust previously reported by some researchers. For example, Vardon et al. investigated the hydrothermal liquefaction of three waste feedstocks including *Spirulina* algae, swine manure and digested anaerobic sludge at 300° C., 30 min reaction time and 10-12 MPa pressure. The bio-oil from sludge with TS=26% was found to have the highest molecular weight (3470 g/mol) [13]. Table 9 presents some of the results for the molecular weight of bio-oils from literature. It seems higher solids concentration gives rise to higher molecular weight bio-oil possibly due to more polymeric reactions. Although, lignin content of algae is much lower than wood sawdust, high solids concentration used in HTL experiments probably has caused the production of higher molecular weight bio-oil. The lower molecular weight of CS-WAS bio-oil indicates the production of lighter compounds as a result of chemical reaction between WAS and lignocellulosic biomass. More detailed characterization of the bio-oil such as chemical components, functional groups, thermal stability etc. will be discussed in the next sections.

Higher Heating Values

The elemental analysis of bio-crude oils and solid residues produced with different feedstocks and their higher heating values (HHV) are presented in Table 10. The results for HTL of only WAS or sawdust are also listed for comparison. The carbon contents of the bio-crude oils from the mixtures (69.1-72.4%) are much higher than that of the original biomass materials (38-47.6%).

In addition the oxygen contents of the oils are 16.3-22.1%, much lower compared to 24.4-45.9% in the feedstocks, resulting in increased higher heating values of the oils. The bio-crude oil products have HHV of 26.4-32.4 MJ/kg in contrast to only 14.6-16.9 MJ/kg for the raw feedstocks. The type of feedstock has a great influence on H/C and O/C ratios of bio-crude oils. The O/C molar ratios of bio-oils from the mixture of WAS and lignocellulosic biomass lie between the O/C ratios of bio-oils from only WAS and BS with much lower O/C ratios and higher H/C ratios for BS-WAS and NP-WAS compared to the O/C and H/C ratio of the bio-oil from BS. BS-WAS and NP-WAS show similar compositions and thus have similar higher heating values, however the bio-oil from CS-WAS has higher oxygen and lower hydrogen content resulting in lower HHV. Generally, the H/C molar ratio of the oils (0.85-1.26) decreased compared to initial H/C ratio of the feeds (1.57-1.65). A lower H/C molar ratio indicates the dehydrogenation reactions such as dehydrogenation of alcohols and amines and production of aldehydes and ketones.

Thus, the presence of these compounds as well as carboxylic acid derivatives as a result of dehydrogenation of aldehydes is expected in the bio-oils. Lower H/C molar ratios also suggest a high degree of unsaturated structures in the oils. The O/C ratio for all of the produced oils (0.17-0.24) is much lower than that of the biomass feed (0.48-0.75 from Table 2), suggesting occurrence of deoxygenation reactions (dehydration or decarboxylation reactions) of the reaction intermediates during the hydrothermal liquefaction, resulting in the production of WSP and $CO_2$ in the gaseous products [28]. Significant amounts of water (50-60 wt %) were formed as the WSP in the experiments. Also the main component of the gas product was $CO_2$ according to Micro-GC analysis. This suggests that the oxygen in biomass is predominantly removed in the form of $CO_2$ and WSP during the liquefaction process.

The elemental composition of solid residues shows that hydrogen content of chars was in the range of 2.2% to 3.9%. Carbon existed in chars mainly in the form of coke with the content of 25.3% to 50.7%. The H/C molar ratio of the chars was 0.92-1.1, suggesting the presence of mainly aromatic compounds. In addition the oxygen existed mainly in the ash components, combined with metal elements in the form of metal oxides which were inactive during the whole process.

Comparing these solids with the solid residue from sawdust experiment, indicates that although there are higher H/C values, and substantially lower oxygen content, the heating values are lower due to high ash present in the solid resides from the co-feeds. The solid residues could be used as energy source for other plant operations. However, the ash should be removed from the solids before they can be used for as solid fuels for heat generation since ash remains as a residue after incineration and high ash content can cause serious corrosion problems.

The elemental composition of the bio-crude oil produced from sawdust with the bio-crude oil with the oils obtained from co-feeding (except for cornstalk and WAS experiment) indicates an improvement in carbon and hydrogen content of the oils and a drop in the oxygen content which subsequently leads to a substantial increase in the heating value of the oils when the mixture is used. This is probably due to the synergetic effect due to presence of WAS as the bio-oil from the waste activated sludge has a very high C carbon and hydrogen content and substantially low percentage of oxygen compared to the bio-oil from sawdust. The H/C molar ratio of 1.1 for the bio-oil from sawdust indicates the presence of aromatic compounds and thus higher viscosity for this oil. Another important difference is the higher concentration of nitrogen and presence of sulfur in the oils produced with the co-feeds. This is due to high levels of sulfur and nitrogen in WAS compared to other types of feedstock according to Table 2 which is also present in the oil from WAS. The high protein content of WAS carried over into the bio-crude oils and resulted in high nitrogen contents (3.1-3.6%) compared to the nitrogen content of the oil produced with sawdust (0.1%) as well as higher sulfur content.

However, the sulfur content is still relatively low compared to many petroleum crudes with the sulfur range of 0.1% to 3% [29]. The nitrogen and oxygen contents of the oils are still too high compared to the petroleum oil that has 0.05-1.5% of oxygen and 0.01-0.7% of nitrogen. The heteroatom content is the main factor that distinguishes the bio-crude oils from petroleum oils [13], [16]. To improve the quality of these bio-oils, further upgrading processes would be needed to further reduce the oxygen content and acid content.

To have a better understanding of the feedstock, carbon distribution in the products, material balance of the process was performed by carbon balance and is presented in Table 11. The carbon composition of bio-crude oils and solid residues were determined by elemental analysis and the carbon content of the WSP and gas products were obtained by total organic carbon (TOC) and Micro-GC analysis, respectively. Carbon recovery was calculated based on the % mass of carbon in the products in relation to the mass of carbon in dried feedstock. The total carbon recovery was in the reasonable range of 89-99% as shown in Table 11.

As indicated above, the largest portion of the carbon in feedstock was transferred to the bio-crude oil. A smaller portion ended up in water soluble product and only a very small fraction was transferred to the solid. The best carbon recovery (99.66%) was obtained with BS-WAS. Inferior mass balance in some tests, is probably due to the loss of some low boiling point and low molecular weight organics during the evaporation process for collection of bio-crude oil products [30], [31].

Bio-Crude Oils Functional Groups

Figure 4:
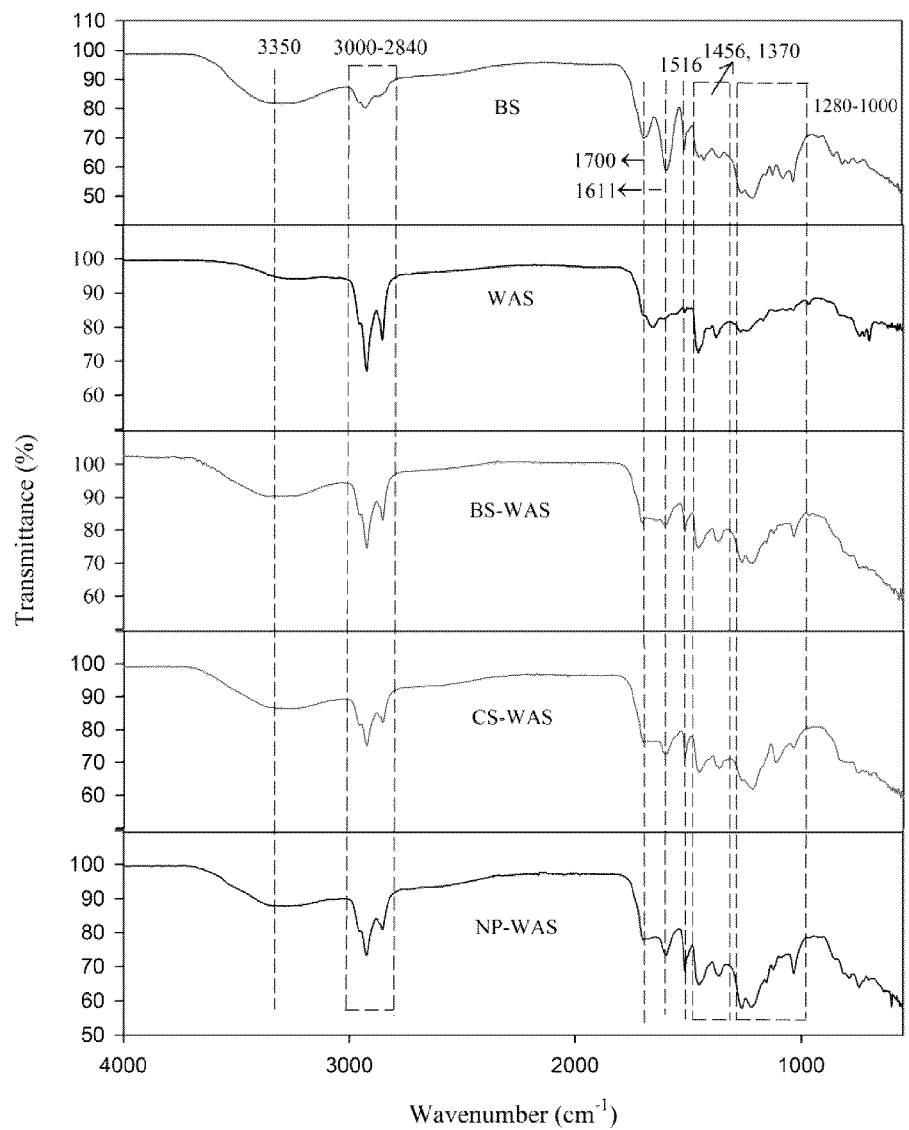
FIG. 4 shows FT-IR spectra of bio-oils produced from co-liquefaction of WAS and liqnocellulosic biomass

FT-IR analysis of the bio-crude oils in the range of 4000-550 $cm^{-1}$ was performed to identify the functional groups and the results are shown in FIG. 4. All bio-oils show similar functional groups regardless of the type of biomass. The difference is only in the intensity of the peaks. The broad absorption at 3350 $cm^{-1}$ is typical of O—H stretching suggesting the presence of alcohols, phenols, carboxylic acids, and water residues in the bio-crude oil. It is also attributed to the N—H stretch of protein group. The bands between 3000 and 2840 $cm^{-1}$ represent C—H stretching vibrations indicating the presence of alkyl C—H. According to FIG. 4, the intensity of these peaks for the oils produced with the co-feeds is stronger than the oil from sawdust indicating that more alkyl groups are present in these oils. However, they are weaker compared to the oil from WAS suggesting that this oil has much larger amounts of alkyl groups. The absorbance at 1700 $cm^{-1}$ represents the C=O stretching vibration of carbonyl groups and indicates the presence of ketones, aldehydes, and carboxylic acids in the oils. The peaks at 1611 $cm^{-1}$, 1516 $cm^{-1}$ and 1456 $cm^{-1}$ represent aromatic ring and its derivatives. The intensity of these peaks, especially the ones at 1611 $cm^{-1}$ and 1516 $cm^{-1}$ is stronger in the oil from sawdust indicating that this oil contains more of these compounds. The bands between 1280 and 1000 $cm^{-1}$ can be attributed to C—O vibrations suggesting the possible presence of acids, phenols or alcohols in the bio-oil. The two absorptions at 1370 and 1456 $cm^{-1}$ are attributed to the bending peaks of methyl (—$CH_3$) and methylene (—$CH_2$) groups, respectively.

Chemical Composition of the Bio-Crude Oils

The oil products were characterized by GC-MS for identification of their chemical compositions. It should be noted that only a fraction of the products formed by HTL are identifiable by GC-MS due to the high molecular weights and boiling point distributions of the bio-oils and the temperature limit of the instrument (maximum boiling point detected 300° C.). Furthermore, some low boiling point compounds may have been masked by the solvent peak or lost when evaporating the acetone used to recover the bio-crude oil [13].

Nitrogenous compounds, fatty acids and phenols make the major fraction of the bio-oils from BS-WAS and NP-WAS, while the largest fraction of the bio-oil from CS-WAS are esters followed by fatty acids and nitrogenous compounds. Other components such as alkanes, alcohols, amines, amide, benzene compounds, carboxylic acids and ketones were identified in the oils. The highest fraction of phenolic compounds were found in BS-WAS oil sample followed by NP-WAS and CS-WAS samples. Phenolic compounds such as 2-methoxy-phenol and 4-ethyl-2-methoxy-phenol were primarily originated from the degradation of lignin components by cleavage of the aryl ether linkages in lignin. They can also be derived from carbohydrates and protein fraction [16]. Cornstalk typically has lower lignin content compared to sawdust and newspaper. Thus the oil from CS-WAS had the lowest amount of phenolic compounds among the other oils. Protein content of WAS resulted the production of bio-crude oils with a high percentage of nitrogenous compounds.

The presence of these compounds such as 1-Dodecamine, 2-methyl-propanamide and 1-acetyl-4-[1-piperidyl]-2-butynone in oils shows that proteins were degraded as a result of hydrothermal liquefaction through decarboxylation and rearrangement of amino acids. The nitrogen-containing organic compounds might react with sugars to form pyridines via the Maillard reaction [32]. Presence of pyridine in the bio-oils samples confirms the occurrence of this reaction. Esters made the major components of the oil obtained from the CS-WAS. Decomposition of furan derivatives which are originated from the decomposition of cellulose may contribute to the formation of esters. All of the oils had considerable fraction of fatty acids which are produced from decomposition of lipids in WAS.

Comparing the components of these oils with the oils from sawdust alone and WAS alone, shows that the oil produced with the mixture of WAS and lignocellulosic biomass has much less phenolic compounds than the oil from sawdust, considerably higher amounts of esters compared to the oils from sawdust alone and WAS alone, and much higher percentage of fatty acids, nitrogenous compounds and saturated compounds compared to the oil from sawdust. The lower phenolic fraction in the oils could be attributed to the lower lignin content of the sewage sludge. The contents of benzene and benzene derivatives were very low in the oils produced with the mixture of WAS and lignocellulosic biomass, far lower than that of the phenolic compounds; however, they were still higher than the oil from sawdust, suggesting that the —OH of phenols on the benzene ring was more easily removed in the reactions with the mixture of WAS and lignocellulosic biomass. The total percentage of aromatics including benzene derivatives, phenols and benzaldehyde is much higher in the oil produced with sawdust compared to the oil from co-feeds which was also confirmed in the FT-IR analysis.

Thermal Gravimetric Analysis

Thermal stability of the feedstocks and oils was measured by TGA. The samples were oven dried at 60° C. for an hour before the analysis. They were then heated from 40 to 900° C. under $N_2$ atmosphere on a thermal gravimetric analyzer and the weight loss (TG) and the rate of weight loss (DTG) of the samples were recorded continuously. The gas was then switched to air and the samples were burned in the air at 900° C. for 20 minutes to determine their fixed carbon (FC) and ash content.

Thermal Gravimetric Analysis for the Feedstocks

Figure 5A:
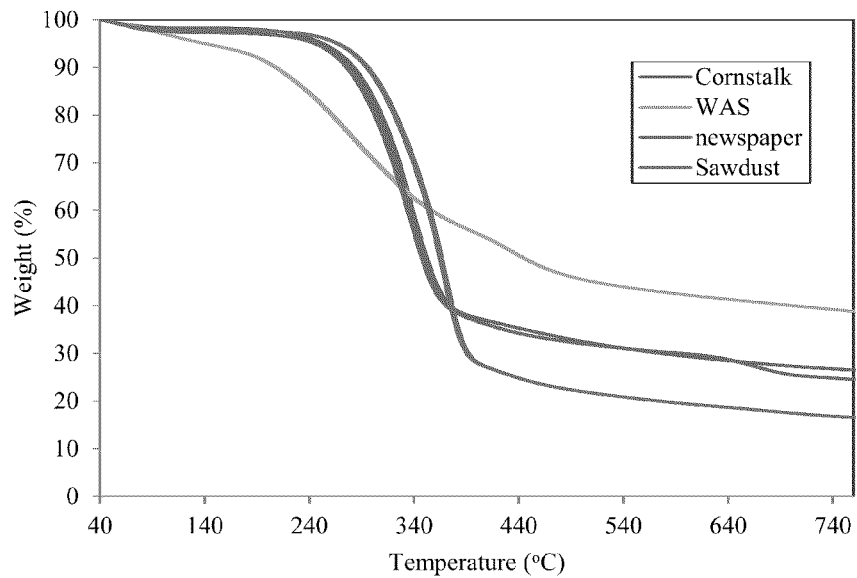
FIG. 5A shows thermogravimetric analysis (TGA) curves for the feedstocks used in the present examples.
Figure 5B:
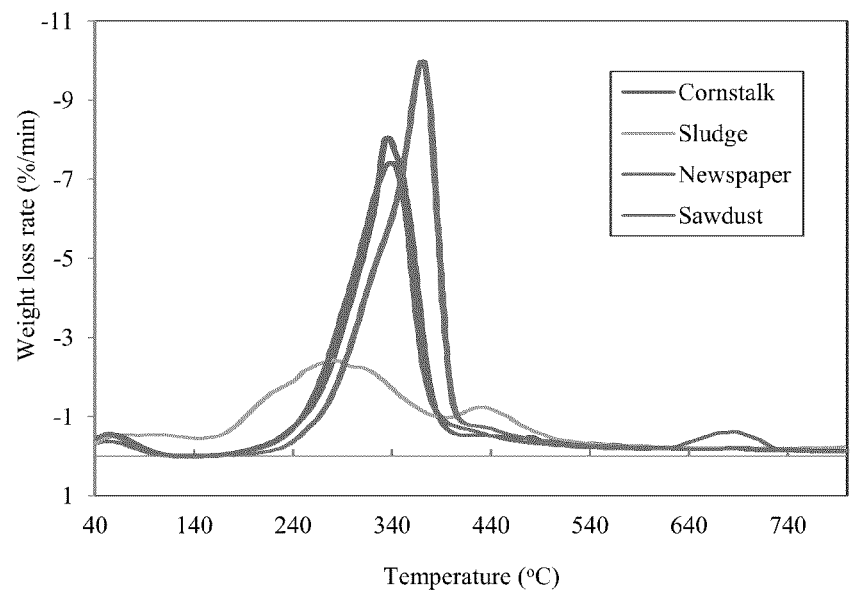
FIG. 5B shows differential thermal analysis (DTA) curves for the feedstocks used in the present examples.

The TG and DTG curves for the different feedstocks are shown in FIG. 5. All three lignocellulosic biomass feedstocks had similar decomposition curves (TG) with more weight loss for sawdust due to its higher volatile matter content. However, they were visibly different from the TG graph for WAS. The difference between the sludge profile and lignocellulosic biomass profiles is due to the different organic and inorganic matter characteristics. It is generally known that the biomass materials mainly consist of protein, carbohydrates, lignin and lipids. As already mentioned, sludge mostly consists of proteins, lipids and carbohydrates, while lignocellulosic biomass mostly comprises carbohydrates and lignin. The structure of sawdust, newspaper and cornstalk started to decompose at around 280-300° C. probably related to their hemicelluloses content and then started to degrade more rapidly at 300-400° C. most likely related to their cellulose content. However, the decomposition of the sludge started at around 200° C. which is 80-100° C. less than the lignocellulosic biomass with a shallower steep indicating the lower contents of volatile matter for the sludge. The decomposition curve of the sludge occurs in two phases: the first phase at 200-370° C. is attributed to the presence of biodegradable matters and organic polymers in the cells and the second phase at 370-500° C. is due to the non-biodegradable material such as cellulosic and similar materials.

The difference between thermal decomposition of different feedstock types can also be determined from the shape of the DTG curves. The curve for the feedstock samples shows a slight weight loss peak at temperatures around 100° C. which could be attributed to the dehydration of the remaining moisture and release of light volatile compounds in the samples. The maximum degradation rate for lignocellulosic feedstocks happens at 330-370° C. indicating that the decomposition of cellulose dominates the sample. The relative intensities of the peaks can be related to the global quantities of the component present in the feedstocks. Among the lignocellulosic biomass samples sawdust was found to have the highest cellulose content. There is some indication of lignin from the smaller DTG peaks between 450-500° C. and 620-730° C. which is more stable and has wider degradation temperature of 280-500° C. and 175-800° C. [33]. According to the DTG graph the lignin content of newspaper was much higher compared to the cornstalk or sawdust. The degradation of WAS occurred at two stages: thermal decomposition of proteins and hemicellulose during the first phase (200-370° C.) and thermal decomposition of protein and cellulose during the second phase (370-500° C.). The intensities of the peaks show that WAS has much lower cellulose and hemicellulose content compared to the lignocellulosic biomass.

Thermal Gravimetric Analysis for the Bio-Oils

Figure 6:
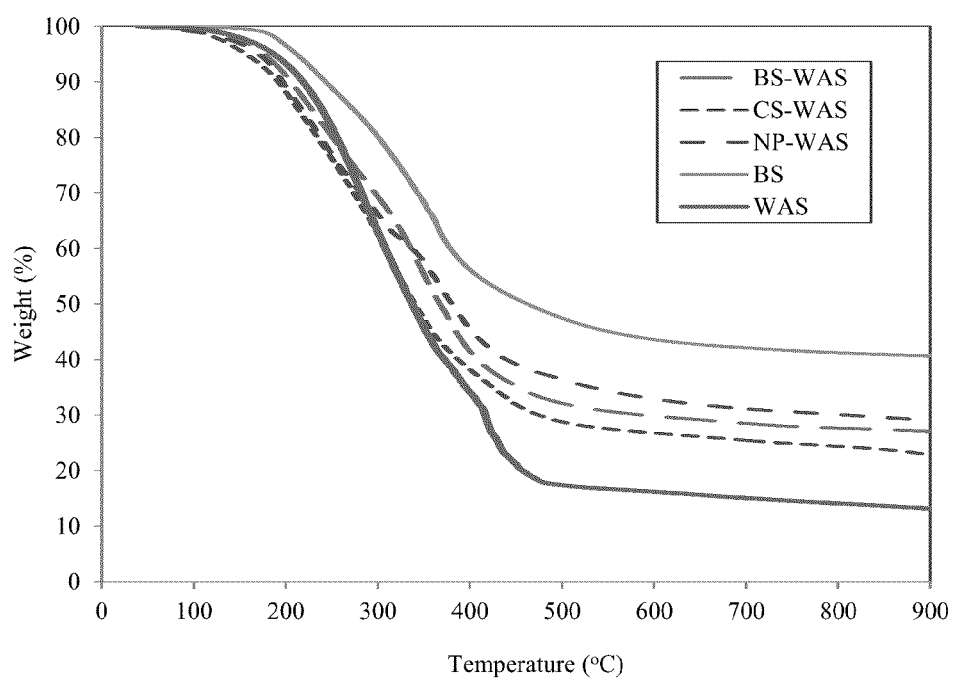
FIG. 6 shows TGA curves for the bio-oils produced using the present process.

The TG and DTG graph of the oils are shown in FIGS. 6 and 7. Some key parameters obtained from the TG/DTG curves, i.e., the initial decomposition, final decomposition and peak temperatures and the contents of volatile matters (VM) and fixed carbon (FC) are presented in Table 12. According to the TG graph there is no substantial difference in thermal stability between the bio oils produced from the mixture of WAS and lignocellulosic biomass. However, the curve for the decomposition of these bio-oils shifted to lower temperatures (161-168° C.) compared to the curve for the bio oil from sawdust (212° C.). It is even lower than the decomposition temperature of bio-oil from WAS (208° C.). This result indicates that they have lower thermal stability and a low activation energy is needed to decompose these oils. They also have higher volatile matter content (71-77%) and lower fixed carbon content (22-28%) compared to the 59.3% of VM and 40.7% of FC for the oil produced from sawdust alone. Since the oil from WAS also shows a very high VM content (86.9%), the enhanced VM content of the bio-oils from mixtures could be due to the synergetic effect when WAS and lignocellulosic biomass are used as a co-feed.

Figure 7A:
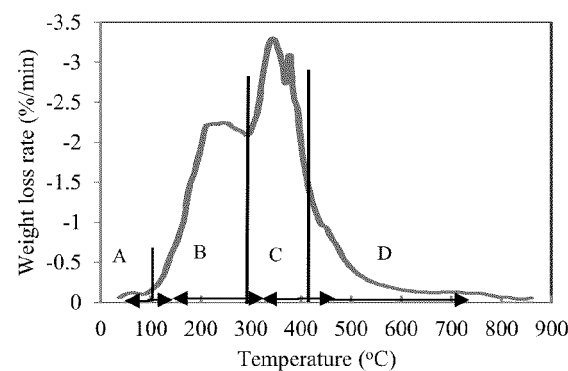
FIG. 7A shows a TGA curve for the bio-oil from the mixture of birchwood sawdust (BS) and waste activated sludge.
Figure 7B:
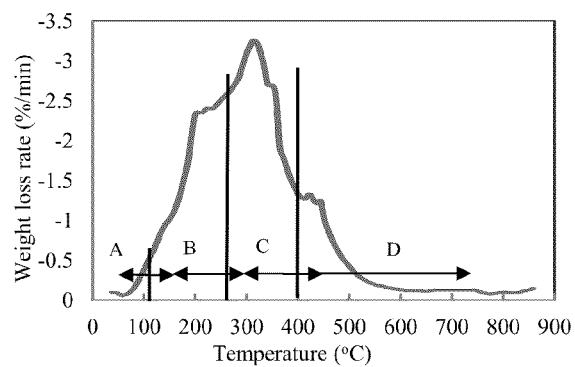
FIG. 7B shows a TGA curve for the bio-oil from the mixture of cornstalk (CS) and waste activated sludge (WAS).
Figure 7C:
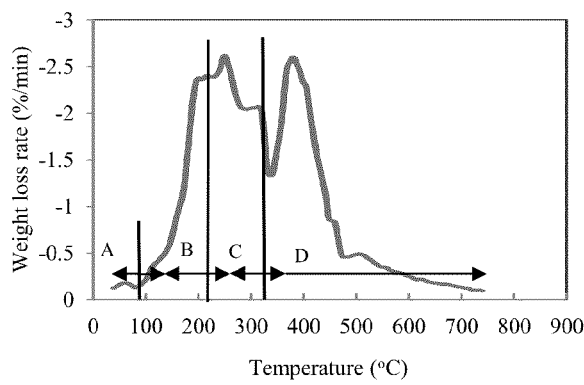
FIG. 7C shows a TGA curve for the bio-oil from the mixture of waste newspaper (NP) and waste activated sludge.

The DTG curve was divided in several stages depending on the rate of weight loss, i.e., stage "A" is the dehydration of superficial moisture and vaporization of light components, stage "B" is the devolatilization and vaporization of low molecular weight material, stage "C" is the polymerization and dehydration and the last stage "D" is the char decomposition phase. The stages and temperature ranges are shown in FIGS. 7A, 7B and 7C. Since the oils were pre-dried in an oven, stage A exhibited a small peak. For BS-WAS and CS-WAS there was a broader range for the volatilization of low molecular weight material starting from around 100° C. to 250-300° C. Thus stage B and C became more distinct compared to NP-WAS. The oil from NP-WAS had lower amount of light components. In stage C polymerization of bio-crude oils into condensed materials such as resin as well as dehydration and condensation of heavy fractions occurs upon heating. BS-WAS and CS-WAS showed higher peaks compared to NP-WAS indicating that more heavy fractions were decomposed for these two oils. The final decomposition stage was broader and accompanied by a very big peak for NP-WAS showing that more char was produced during the heating of this bio-oil in the previous stages.

TGA data can also be used to estimate the boiling range of heavy oils [34]. The boiling point distribution of the bio crude oils is determined using thermal gravimetric analysis data and is presented in Table 13. The weight loss of the samples before 110° C. is an indicator of moisture and is less than 2 wt % for all the oils, revealing that the drying process efficiently removed water. According to Table 13, the percentage of components with lower boiling points has increased for the mixture of WAS and lignocellulosic biomass compared to sawdust alone. Around 30-37 wt % of the bio-oils produced in the presence of WAS have boiling points lower than 300° C. compared to only 19 wt % in the oil produced with sawdust alone. This means that addition of WAS has shifted the molecular distribution to more volatile compounds.

Example 5

Figure 8:
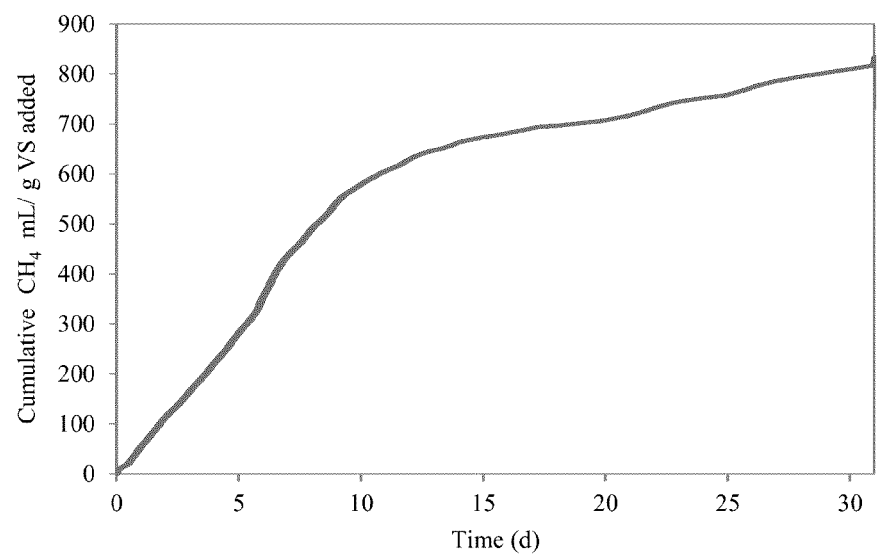
FIG. 8 shows a biochemical methane potential (BMP) result for water-soluble product (WSP).

The water soluble product (WSP) was used for methane production through BMP analysis. BMP is an important and valuable assay to determine the potential of a biomass for anaerobic digestion. The WSP sample was first analyzed for TOC, COD, VS and TS. The WSP had negligible solid concentration. The total solids (TS) and volatile solids (VS) of the sample were 1.52% and 0.84%, respectively and the TOC and COD were 16.33 g/l and 41.86 g/l, respectively, making the COD/TOC ratio of 2.5. This ratio shows the degree of reduction of carbon compounds as a result of HTL treatment. FIG. 8 shows the cumulative methane production from WSP per volatile solids (VS) (g) added. The BMP result shows a rapid initial methane production (no lag phase), peaking at around 800 mL per gram (g) VS added after 31 days. Since 50 mL of the WSP was used for the BMP test, the volume of produced gas is per 0.816 g of total organic carbon (TOC) or 2.09 g of COD. The degradability of the sample measured based on COD was 46%.

Water-soluble products are the largest fraction of by-products from the hydrothermal liquefaction process. Using this by-product directly from the co-liquefaction process without any further treatment to produce biogas is a novel process originated in this research. The results show that considerable amount of biogas can be produced from this by-product, making the co-production of biogas and bio-oil feasible. The produced biogas can be used to generate electricity and heat, wherein the energy produced can be re-invested back into the process.

Conclusion

A process based on hydrothermal liquefaction (HTL) treatment for co-processing of high-water-content wastewater sludge and other lignocellulosic biomass for co-production of biogas and bio-crude oil has been disclosed herein. The operating conditions including reaction temperature, reaction time and solids concentration have been optimized based on the response surface methodology for the maximum bio-crude oil production. Three types of lignocellullosic waste biomass (birchwood sawdust (BS), waste newspaper (NP), and cornstalk (CS)) were mixed with waste activated sludge (WAS) and converted to bio-crude oil at the optimized operating conditions. These waste biomass materials are exemplary only the present process is not restricted to them.

Co-conversion of waste activated sludge and other waste biomass is a beneficial method for converting two types of waste materials into value-added products at the same time with the advantage of producing higher quality bio-crude oil compared to lignocellulosic biomass. The molecular weight of the bio-oils produced was significantly reduced (448-562 g/mol) when sludge was mixed with the lignocellulosic biomass compared to the bio-oil from sawdust (856 g/mol) indicating the synergetic effect of WAS and lignocellulosic biomass resulting in the presence of lighter components in the bio-oils.

According to the Van Krevelen diagram, bio-oils from co-feeding presented lower H/C and O/C ratios suggesting the occurrence of dehydrogenation and deoxygenation reactions which results in higher quality of bio-crude oils. According to GC-MS results the oils produced from co-feeding have much less phenolic compounds, considerably higher amounts of esters, fatty acids, and nitrogenous compounds compared to the oil produced from sawdust.

The bio-oils produced with co-feeds had higher volatile matter content and lower fixed carbon compared to the bio-oil produced from sawdust. They also showed lower thermal stability and consequently lower activation energy for decomposition. The boiling point analysis of these oils indicated the presence of 30-37 wt % low molecular weight compounds (<300° C.) compared to only 19 wt % in the oil produced with sawdust which resulted in a significant lower molecular weight of these oils.

The two by-products of the process can be used to generate heat and electricity. The solid residues or bio-chars can be used as solid fuels for heat generation. The WSP can be used to produce biogas anaerobic digestion. The BMP test showed that 800 mL bio-methane was produced cumulatively in 30 days per 0.816 g of total organic carbon (TOC) or 2.09 g of chemical oxygen demand (COD) of water-soluble products.

The present process is significantly different from the previous wastewater HTL processes for several reasons. First, the present process aims at co-production of biogas and bio-crude oil. Co-processing wastewater sludge (more than 90% water content) with other waste materials such as sawdust, cornstalk, MSW, etc. are employed to adjust substrate concentration to an optimum value and hence to enhance economics of the process. Moreover, this enables the process to treat two types of waste biomass at the same time. The yields of bio-crude oil from this process are significantly greater than that of the STORS process In addition, the co-production process disclosed herein uses the by-product of HTL (water-soluble product) for biogas production which is different from the Cambi or BioThelys processes in which the sludge is used for anaerobic digestion and biogas production. No drying or dewatering is required in the present process for processing the water-soluble product compared to Cambi or BioThelys processes, providing cost advantage by eliminating the costly process of drying.

Further, the quality of HTL bio-oil for liquid fuel use is higher than fast pyrolysis oil, with lower moisture and higher energy content.

Finally, the process by-products can be easily used, for example the solid biochar can be an energy source for other plant operations or can be sold, and a water soluble stream can be used for biogas production through anaerobic digestion or recycled back into the water treatment process.

TABLES

TABLE 1

| Experimental variables | Symbol | Coded level of variables | | | | |
| --- | --- | --- | --- | --- | --- | --- |
| | | −1.682 | −1 | 0 | 1 | 1.682 |
| Temperature (° C.) | $X_1$ | 200 | 230 | 275 | 320 | 350 |
| Reaction time (min) | $X_2$ | 10 | 20 | 35 | 50 | 60 |

TABLE 1-continued

| Experimental variables | Symbol | Coded level of variables | | | | |
|---|---|---|---|---|---|---|
| | | −1.682 | −1 | 0 | 1 | 1.682 |
| Solids concentration (wt %) | $X_3$ | 5 | 7 | 10 | 13 | 15 |

Experimental variables and levels

TABLE 2

Characteristics of the feedstocks

| Parameter | Birchwood sawdust | Cornstalk | Newspaper | WAS |
|---|---|---|---|---|
| Proximate analysis | | | | |
| Volatile matter (VM)[a,b] (wt %) | 83.45 | 74.08 | 76.14 | 62.24 |
| Fixed carbon (FC)[a,b] (wt %) | 16.32 | 15.21 | 14.64 | 14.09 |
| Ash[a] (wt %) | 0.23 | 10.71 | 9.22 | 23.67 |
| Moisture (wt %) | 0[c] | 0[c] | 0[c] | 96.1 |
| pH | — | — | — | 7.76 |

TABLE 2-continued

Characteristics of the feedstocks

| Parameter | Birchwood sawdust | Cornstalk | Newspaper | WAS |
|---|---|---|---|---|
| Ultimate analysis[a] | | | | |
| C (wt %) | 47.6 | 42.8 | 42.1 | 38.04 |
| H (wt %) | 6.3 | 5.7 | 5.5 | 5.23 |
| N (wt %) | 0 | 0.46 | 0 | 7.20 |
| S (wt %) | 0 | 0 | 0 | 0.75 |
| O[d] (wt %) | 45.9 | 39.8 | 42.2 | 24.4 |
| H/C | 1.59 | 1.60 | 1.57 | 1.65 |
| N/C | 0 | 0.01 | 0 | 0.16 |
| O/C | 0.72 | 0.70 | 0.75 | 0.48 |
| HHV[e] (MJ/kg) | 16.9 | 15.5 | 14.6 | 16.0 |

[a]On a dry basis
[b]Determined by TGA at 800° C. in nitrogen and air atmosphere
[c]Raw material was dried in oven at 105° C. for 24 hr before the experiments
[d]Calculated by difference (100% − C % − H % − N % − S % − Ash %)
[e]Higher Heating Value (HHV) calculated by Dulong formula, i.e., HHV (MJ/kg) = 0.3383C + 1.422(H − O/8)

TABLE 3

Concentration of major inorganic elements in feedstocks' ash detected by ICP-AES

| | Sawdust (wt %) | Cornstalk (wt %) | Newspaper (wt %) | WAS (wt %) |
|---|---|---|---|---|
| Aluminum (Al) | 0.76 | 0.51 | 2.39 | 0.75 |
| Barium (Ba) | 0.02 | 0.01 | 0.01 | 0.09 |
| Calcium (Ca) | 13.27 | 8.11 | 21.81 | 9.87 |
| Chromium (Cr) | Nd | 0.02 | Nd | 0.03 |
| Copper (Cu) | 0.02 | 0.01 | 0.04 | 0.23 |
| Iron (Fe) | 0.68 | 0.65 | 0.19 | 25.36 |
| Potassium (K) | 12.19 | 19.61 | 0.06 | 2.18 |
| Magnesium (Mg) | 2.74 | 2.34 | 0.53 | 1.47 |
| Manganese (Mn) | 0.43 | 0.04 | Nd | 0.25 |
| Sodium (Na) | 2.01 | 0.26 | 1.37 | 2.91 |
| Nickel (Ni) | Nd | 0.01 | Nd | Nd |
| Silicon (Si) | 0.07 | 0.03 | 0.04 | 1.21 |
| Zinc (Zn) | 0.19 | 0.03 | 0.01 | 0.16 |

Nd: Not detected

TABLE 4

Optimum operating conditions

| Temp. (° C.) | Reaction time (min) | Concentration (wt %) | Oil yield (wt %) | | Solid residue yield (wt %) | |
|---|---|---|---|---|---|---|
| | | | Predicted | Experimental | Predicted | Experimental |
| 310 | 10 | 10 | 33.55 | 33.73 ± 0.98 | 16.51 | 15.51 ± 0.72 |

Optimum operating conditions, predicted and experimental oil and solid yields

TABLE 5

Products distribution and molecular weight of the bio-crude oils from HTL of CS-WAS in the presence of KOH at 310° C., 10 min and 10 wt % solid concentration

| Feedstock | Oil yield (wt %) | Solid yield (wt %) | WSP yield (wt %) | Conversion (wt %) | MW (g/mol) |
|---|---|---|---|---|---|
| CS-WAS | 34.19 ± 2.3 | 6.36 ± 1.1 | 59.40 ± 1.3 | 93.6 ± 1.1 | 448 |

TABLE 6

Products distribution and molecular weight of the bio-crude oils from HTL of NP-WAS in the presence of KOH at 310° C., 10 min and 10 wt % solid concentration

| Feedstock | Oil yield (wt %) | Solid yield (wt %) | WSP yield (wt %) | Conversion (wt %) | MW (g/mol) |
|---|---|---|---|---|---|
| NP-WAS | 28.78 ± 0.6 | 10.31 ± 0.1 | 60.86 ± 0.7 | 89.7 ± 0.1 | 562 |

TABLE 7

Products distribution and molecular weight of the bio-crude oils from BS and WAS in the presence of KOH at 310° C., 10 min and 10 wt % solid concentration

| Feedstock | Oil yield (wt %) | Solid yield (wt %) | WSP yield (wt %) | Conversion (wt %) | MW (g/mol) |
|---|---|---|---|---|---|
| WAS | 23.11 ± 3.8 | 13.15 ± 1.7 | 63.68 ± 5.5 | 86.8 ± 1.7 | 415 |
| BS[1] | 39.5 ± 2.8 | 12.0 ± 1.2 | 48.2 ± 3.9 | 87.9 ± 1.2 | 856 |

[1]Result taken from previous study by the authors at almost the same operating conditions (300° C., 30 min and 10 wt % solid concentration)

TABLE 8

| Feedstock | Oil yield (wt %) | Solid yield (wt %) | WSP yield (wt %) | Conversion (wt %) | MW (g/mol) |
|---|---|---|---|---|---|
| WAS + sawdust | 31.90 | 2.94 | 64.92 | 97.06 | 431 |

TABLE 9

Molecular weight of bio-oils produced from sludge or lignocellulosic biomass

| Feedstock | HTL operating conditions | Mw (g/mol) | Ref. |
|---|---|---|---|
| Pinewood sawdust | Temperature: 300° C., Reaction time: 15 min, Solvent to biomass ratio: 10, Nitrogen atmosphere | 1373 | [26] |
| Algal biomass | Temperature: 300° C., Reaction time: 30 min, Solid concentration: 20%, Nitrogen atmosphere | 1860-3980 | [27] |
| Anaerobic sludge | Temperature: 300° C., Reaction time: 30 min, Solid concentration: 26%, Nitrogen atmosphere | 3470 | [13] |

TABLE 10

| | Bio-crude oils | | | | | | | | Solid residues | | | | | |
|---|---|---|---|---|---|---|---|---|---|---|---|---|---|---|
| Feedstock | C (%) | H (%) | N (%) | S (%) | O (%)[a] | H/C (—) | O/C (—) | HHV (MJ/kg)[b] | C (%) | H (%) | N (%) | S (%) | H/C (—) | O and metal elements[a] |
| BS-WAS | 72.1 | 7.5 | 3.1 | 0.1 | 17.0 | 1.25 | 0.18 | 32.0 | 50.7 | 3.9 | 2.6 | 0.1 | 0.92 | 42.7 |
| CS-WAS | 69.1 | 4.9 | 3.6 | 0.1 | 22.1 | 0.85 | 0.24 | 26.4 | 25.3 | 2.2 | 1.8 | 0 | 1.04 | 70.7 |
| NP-WAS | 72.4 | 7.6 | 3.4 | 0.2 | 16.3 | 1.26 | 0.17 | 32.4 | 33.9 | 3.1 | 1.8 | 0 | 1.10 | 61.2 |
| BS[c] | 66.5 | 6.1 | 0.1 | 0 | 27.3 | 1.10 | 0.31 | 26.3 | 69.8 | 4.5 | 0.2 | 0 | 0.77 | 25.5 |
| WAS | 76.3 | 9.3 | 5.5 | 0.4 | 7.8 | 1.46 | 0.08 | 37.7 | 18.8 | 2.1 | 1.7 | 0.1 | 1.34 | 77.3 |

Elemental composition of bio-crude oils and solid residues obtained from liquefaction with/without catalyst at 310° C. for 10 min.
[a]Calculated by difference (100% − C % − H % − N % − S %);
[b]Higher Heating Value (HHV) calculated by Dulong formula, i.e., HHV (MJ/kg) = 0.3383C + 1.422(H—O/8)
[c]Result taken from previous study by the authors at almost the same operating conditions (300° C., 30 min and 10 wt % solid concentration)

TABLE 11

Carbon recovery in the products from liquefaction at 310° C. for 10 min.

| Sample | Oil (%) | Solid (%) | WSP (%) | Gas (%) | Total C (%) |
|---|---|---|---|---|---|
| BS-WAS | 54.03 | 17.54 | 28.07 | 0.01 | 99.66 |
| CS-WAS | 56.92 | 3.91 | 35.99 | 0.03 | 96.86 |
| NP-WAS | 50.82 | 8.54 | 30.34 | 0.03 | 89.74 |

TABLE 12

| Oil | Ignition temperature ° C. ($T_i$) | Burnout temperature ° C. ($T_b$) | DTG peak temperature ° C. ($T_m$) | VM (wt %) | FC (wt %) | Ash (wt %) |
|---|---|---|---|---|---|---|
| BS-WAS | 168 | 883 | 344 | 73.1 | 26.8 | 0.18 |
| CS-WAS | 161 | 880 | 314 | 77.4 | 22.4 | 0.18 |
| NP-WAS | 164 | 892 | 250, 380 | 71.1 | 28.8 | 0.08 |
| BS | 212 | 882 | 367 | 59.3 | 40.7 | NG |
| WAS | 208 | 890 | 284, 419 | 86.9 | 12.3 | 0.71 |

Decomposition start/peak/end temperatures, volatile matter, and fixed carbon of bio-crude oils

TABLE 13

Estimated boiling point distribution of bio-crude oils (%)

| Distillate range (° C.) | Bio-oils | | | | |
|---|---|---|---|---|---|
| | BS-WAS | CS-WAS | NP-WAS | Sawdust | WAS |
| 40-110 | 0.78 | 1.22 | 1.19 | 0.13 | 0.58 |
| 110-200 | 8.03 | 10.56 | 9.61 | 3.29 | 6.09 |
| 200-300 | 21.82 | 25.65 | 23.02 | 16.41 | 30.24 |
| 300-400 | 27.88 | 24.38 | 20.65 | 23.97 | 28.98 |
| 400-550 | 10.79 | 10.71 | 11.18 | 11.12 | 17.40 |
| 550-700 | 2.19 | 2.04 | 3.26 | 2.97 | 1.63 |
| 700-800 | 0.87 | 1.09 | 1.01 | 0.88 | 0.98 |
| 800-900 | 0.60 | 1.57 | 1.07 | 0.56 | 0.95 |

REFERENCES

[1] P. Azadi, E. Afif, H. Foroughi, T. Dai, F. Azadi, and R. Farnood, "Catalytic reforming of activated sludge model compounds in supercritical water using nickel and ruthenium catalysts," *Appl. Catal. B Environ.*, vol. 134-135, pp. 265-273, May 2013.

[2] E. Neyens, J. Baeyens, and C. Creemers, "Alkaline thermal sludge hydrolysis.," *J. Hazard. Mater.*, vol. 97, no. 1-3, pp. 295-314, 2003.

[3] E. Neyens, J. Baeyens, R. Dewil, and B. De Heyder, "Advanced sludge treatment affects extracellular polymeric substances to improve activated sludge dewatering," *J. Hazard. Mater.*, vol. 106, no. 2-3, pp. 83-92, 2004.

[4] C. He, A. Giannis, and J.-Y. Wang, "Conversion of sewage sludge to clean solid fuel using hydrothermal carbonization: Hydrochar fuel characteristics and combustion behavior," *Appl. Energy*, vol. 111, pp. 257-266, November 2013.

[5] V. K. Tyagi and S.-L. Lo, "Sludge: A waste or renewable source for energy and resources recovery," *Renew. Sustain. Energy Rev.*, vol. 25, no. 71, pp. 708-728, September 2013.

[6] P. M. Molton, A. G. Fassbender, and M. D. Brown, "STORS: The Sludge-to-Oil Reactor System," Cincinnati, Ohio, 1986.

[7] W. L. Kranich and A. E. Eralp, "Conversion of Sewage Sludge to Oil by Hydroliquefaction," Cincinnati, Ohio, 1984.

[8] C. Xu and J. Lancaster, "Conversion of secondary pulp/paper sludge powder to liquid oil products for energy recovery by direct liquefaction in hot-compressed water.," *Water Res.*, vol. 42, no. 6-7, pp. 1571-1582, March 2008.

[9] Y. Kalogo and H. Monteith, "State of Science Report: Energy and Resource Recovery from Sludge," 2008.

[10] L. Nazari, Z. Yuan, S. Souzanchi, M. B. Ray, and C. (Charles) Xu, "Hydrothermal Liquefaction of Woody Biomass in Hot-compressed Water: Catalyst Screening and Comprehensive Characterization of Bio-crude Oils," *Fuel*, vol. 162, pp. 74-83, 2015.

[11] N. Bradley, "The Response Surface Methodology (thesis)," Indiana University South Bend, 2007.

[12] J. N. Sahu, J. Acharya, and B. C. Meikap, "Response surface modeling and optimization of chromium (VI) removal from aqueous solution using Tamarind wood activated carbon in batch process," *J. Hazard. Mater.*, vol. 172, no. 2-3, pp. 818-825, 2009.

[13] D. R. Vardon, B. K. Sharma, J. Scott, G. Yu, Z. Wang, L. Schideman, Y. Zhang, and T. J. Strathmann, "Chemical properties of bio-crude oil from the hydrothermal liquefaction of Spirulina algae, swine manure, and digested anaerobic sludge.," *Bioresour. Technol.*, vol. 102, no. 17, pp. 8295-8303, September 2011.

[14] American Public Health Association (APHA), "Standard Methods for the Examination of Water and Wastewater," 20th ed., Washington, D.C., USA, 1960.

[15] C. Tian, B. Li, Z. Liu, Y. Zhang, and H. Lu, "Hydrothermal liquefaction for algal biorefinery: A critical review," *Renew. Sustain. Energy Rev.*, vol. 38, pp. 933-950, 2014.

[16] H. Huang, X. Yuan, H. Zhu, H. Li, Y. Liu, X. Wang, and G. Zeng, "Comparative studies of thermochemical liquefaction characteristics of microalgae, lignocellulosic biomass and sewage sludge," *Energy*, vol. 56, pp. 52-60, July 2013.

[17] B. N. Kuznetsov, S. a. Kuznetsova, V. a. Levdansky, A. V. Levdansky, N. Y. Vasil'eva, N. V. Chesnokov, N. M. Ivanchenko, L. Djakovitch, and C. Pinel, "Optimized methods for obtaining cellulose and cellulose sulfates from birch wood," *Wood Sci. Technol.*, vol. 49, no. 4, pp. 825-843, 2015.

[18] G. Shulga, S. Vitolina, V. Shekels, L. Belkova, G. Cazacu, C. Vasile, and L. Nita, "Lignin Separated from the Hydrolyzate of the Hydrothermal Treatment of Birch Wood and Its Surface Properties," *Cellul. Chem. Technol.*, vol. 46, no. 5-6, pp. 307-318, 2012.

[19] Z. Daud, M. Zainuri, M. Hatta, A. Sari, M. Kassim, H. Awang, A. M. Aripin, V. Education, U. Tun, and H. Onn, "Analysis the Chemical Composition and Fiber Morphology Structure of Corn Stalk," vol. 7, no. 9, pp. 401-405, 2013.

[20] J. Flandez, I. González, J. B. Resplandis, N. E. El Mansouri, F. Vilaseca, and P. Mutjé, "Management of corn stalk waste as reinforcement for polypropylene injection moulded composites," *BioResources*, vol. 7, no. 2, pp. 1836-1849, 2012.

[21] H. Chen, Q. Han, R. A. Venditti, and H. Jameel, "Enzymatic Hydrolysis of Pretreated Newspaper Having High Lignin Content for Bioethanol Production," vol. 10, no. 3, pp. 4077-4098, 2015.

[22] L. Zhang, P. Champagne, and C. (Charles) Xu, "Bio-crude production from secondary pulp/paper-mill sludge and waste newspaper via co-liquefaction in hot-compressed water," *Energy*, vol. 36, no. 4, pp. 2142-2150, April 2011.

[23] S. S. Toor, L. Rosendahl, and A. Rudolf, "Hydrothermal liquefaction of biomass: A review of subcritical water technologies," *Energy*, vol. 36, no. 5, pp. 2328-2342, May 2011.

[24] S. Yin, R. Dolan, M. Harris, and Z. Tan, "Subcritical hydrothermal liquefaction of cattle manure to bio-oil: Effects of conversion parameters on bio-oil yield and characterization of bio-oil.," *Bioresour. Technol.*, vol. 101, no. 10, pp. 3657-3664, May 2010.

[25] C. Jazrawi, P. Biller, A. B. Ross, A. Montoya, T. Maschmeyer, and B. S. Haynes, "Pilot plant testing of continuous hydrothermal liquefaction of microalgae," *Algal Res.*, vol. 2, no. 3, pp. 268-277, July 2013.

[26] S. Cheng, "Bio-Based Phenolic Resins and Adhesives Derived from Forestry Rrsidues/Wastes and Lignin (thesis)," Lakehead University, 2011.

[27] D. R. Vardon, B. K. Sharma, G. V Blazina, K. Rajagopalan, and T. J. Strathmann, "Thermochemical conversion of raw and defatted algal biomass via hydrothermal liquefaction and slow pyrolysis.," *Bioresour. Technol.*, vol. 109, pp. 178-87, April 2012.
[28] T. Matsui, A. Nishihara, C. Ueda, and M. Ohtsuki, "Liquefaction of micro-algae with iron catalyst," vol. 76, no. 11, pp. 1043-1048, 1997.
[29] J. Speight, *Handbook of Petroleum Product Analysis.* 2002.
[30] Y. Yang, A. Gilbert, and C. (Charles) Xu, "Production of Bio-Crude from Forestry Waste by Hydro-Liquefaction in Sub-/Super-Critical Methanol," *AIChE J.*, vol. 55, no. 3, pp. 807-819, 2009.
[31] P. Sun, M. Heng, S. Sun, and J. Chen, "Direct liquefaction of *paulownia* in hot compressed water: Influence of catalysts," *Energy*, vol. 35, no. 12, pp. 5421-5429, 2010.
[32] L. Zhang, C. C. Xu, and P. Champagne, "Energy recovery from secondary pulp/paper-mill sludge and sewage sludge with supercritical water treatment.," *Bioresour. Technol.*, vol. 101, no. 8, pp. 2713-21, April 2010.
[33] S. Li, A. Sanna, and J. M. Andresen, "Influence of temperature on pyrolysis of recycled organic matter from municipal solid waste using an activated olivine fluidized bed," *Fuel Process. Technol.*, vol. 92, no. 9, pp. 1776-1782, September 2011.
[34] a. B. Ross, P. Biller, M. L. Kubacki, H. Li, A. Lea-Langton, and J. M. Jones, "Hydrothermal processing of microalgae using alkali and organic acids," *Fuel*, vol. 89, no. 9, pp. 2234-2243, September 2010.

Therefore what is claimed is:

1. A process of coproduction of biogas and bio-crude oil, comprising:
    a) mixing wastewater sludge with waste lignocellulosic biomass to form a mixture with an overall solid content in a range from about 5 to about 25 wt %;
    b) subjecting the mixture to hydrothermal liquefaction in a reactor at held at a temperature in a range from about 200 to about 350° C. under pressure in a range from about 50 to about 150 bars and in the presence of a catalyst to give a reaction product;
    c) removing and collecting solid bio-char from the reaction product in the reactor, removing and collecting bio-oil from the reaction product in the reactor, and removing and collecting aqueous products from the reaction product in the reactor; and
    d) anaerobically digesting the aqueous products to produce and collecting biogas produced from the anaerobically digested aqueous products.

2. The process according to claim 1, wherein the mixture of wastewater sludge and waste biomass has a solid content in a range from about 8 to about 20 wt %.

3. The process according to claim 1, wherein the solid content of the mixture of wastewater sludge and waste biomass is about 10 wt %.

4. The process according to claim 1, wherein the temperature is maintained in a range from about 280 to about 330° C.

5. The process according to claim 1, wherein the pressure is maintained in a range from about 100 to about 150 bars.

6. The process according to claim 1, wherein the catalyst is any one or combination of KOH, $K_2CO_3$, NaOH, $Na_2CO_3$, Colemanite, $FeSO_4$, $Ca(OH)_2$, hydrotalcite (HT), and MgO.

7. The process according to claim 1, wherein the catalyst is any one or combination of KOH, $K_2CO_3$, NaOH and $Na_2CO_3$.

8. The process according to claim 1 performed in a continuous reactor system.

9. The process according to claim 1 performed in a batch reactor system.

10. The process according to claim 2, wherein the temperature is maintained in a range from about 280 to about 330° C.

11. The process according to claim 2, wherein the pressure is maintained in a range from about 100 to about 150 bars.

12. The process according to claim 2, wherein the catalyst is any one or combination of KOH, $K_2CO_3$, NaOH, $Na_2CO_3$, Colemanite, $FeSO_4$, $Ca(OH)_2$, hydrotalcite (HT), and MgO.

13. The process according to claim 2, performed in a continuous reactor system.

14. The process according to claim 2, performed in a batch reactor system.

15. The process according to claim 3, wherein the temperature is maintained in a range from about 280 to about 330° C.

16. The process according to claim 3, wherein the pressure is maintained in a range from about 100 to about 150 bars.

17. The process according to claim 3, wherein the catalyst is any one or combination of KOH, $K_2CO_3$, NaOH, $Na_2CO_3$, Colemanite, $FeSO_4$, $Ca(OH)_2$, hydrotalcite (HT), and MgO.

18. The process according to claim 3, performed in a continuous reactor system.

19. The process according to claim 3, performed in a batch reactor system.

20. The process according to claim 4, wherein the pressure is maintained in a range from about 100 to about 150 bars.

* * * * *